(12) United States Patent
Baldoni et al.

(10) Patent No.: US 11,534,611 B2
(45) Date of Patent: Dec. 27, 2022

(54) THERAPEUTIC MODULATION TO TREAT BLOOD GLUCOSE ABNORMALITIES, INCLUDING TYPE 2 DIABETES, AND/OR REDUCE HBA1C LEVELS, AND ASSOCIATED SYSTEMS AND METHODS

(71) Applicant: Nevro Corp., Redwood City, CA (US)

(72) Inventors: Daniel Baldoni, Redwood City, CA (US); Satinderpall Singh Pannu, Pleasanton, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 16/985,127

(22) Filed: Aug. 4, 2020

(65) Prior Publication Data

US 2020/0360698 A1 Nov. 19, 2020

Related U.S. Application Data

(63) Continuation of application No. 16/369,814, filed on Mar. 29, 2019, now abandoned.

(60) Provisional application No. 62/649,838, filed on Mar. 29, 2018.

(51) Int. Cl.
*A61N 1/36* (2006.01)
*A61N 1/05* (2006.01)

(52) U.S. Cl.
CPC ....... *A61N 1/36189* (2013.01); *A61N 1/0551* (2013.01); *A61N 1/36175* (2013.01); *A61N 1/36007* (2013.01); *A61N 1/36062* (2017.08)

(58) Field of Classification Search
None
See application file for complete search history.

(56) References Cited

U.S. PATENT DOCUMENTS

| 6,721,603 | B2 | 4/2004 | Zabara et al. |
| 6,871,099 | B1 | 3/2005 | Whitehurst et al. |
| 7,162,304 | B1 | 1/2007 | Bradley |

(Continued)

FOREIGN PATENT DOCUMENTS

| WO | WO-2014146082 | 9/2014 |
| WO | WO-2017044904 | 3/2017 |

(Continued)

OTHER PUBLICATIONS

Ahmed et al., "Effects of Spinal Cord Stimulation on Pain Thresholds and Sensory Perceptions in Chronic Pain Patients," Neuromodulation. 2015;18(5):6 pages.

(Continued)

*Primary Examiner* — Michael W Kahelin
*Assistant Examiner* — Elizabeth K So
(74) *Attorney, Agent, or Firm* — Perkins Coie LLP

(57) ABSTRACT

Systems and methods for treating a patient having a blood glucose abnormality, such as type 2 diabetes (T2D), using an electrical signal are disclosed. A representative method for treating a patient includes, based at least in part on a patient indication of a blood glucose abnormality, positioning at least one implantable signal delivery device proximate to a target location at the patient's spinal cord within a vertebral range of from about C8 to about T12. The method further includes directing an electrical signal to the target location via the implantable signal delivery device, wherein the electrical signal has a frequency in a frequency range of from 1.2 kHz to 100 kHz.

34 Claims, 11 Drawing Sheets

(56) References Cited

U.S. PATENT DOCUMENTS

| | | | |
|---|---|---|---|
| 8,569,935 B1 | 10/2013 | Kosierkiewicz | |
| 8,712,533 B2 | 4/2014 | Alataris | |
| 8,768,472 B2 | 7/2014 | Fang | |
| 8,918,190 B2 | 12/2014 | Libbus et al. | |
| 8,954,153 B2 | 2/2015 | Boggs, II | |
| 9,002,477 B2 | 4/2015 | Burnett | |
| 9,278,215 B2* | 3/2016 | Thacker | A61N 1/36071 |
| 9,283,387 B2* | 3/2016 | Thacker | A61N 1/36175 |
| 9,295,839 B2* | 3/2016 | Thacker | A61N 1/36171 |
| 9,295,841 B2 | 3/2016 | Fang et al. | |
| 9,327,121 B2 | 5/2016 | Thacker | |
| 9,387,338 B2 | 7/2016 | Burnett | |
| 9,452,286 B2 | 9/2016 | Cowan et al. | |
| 9,486,632 B2 | 11/2016 | Saab | |
| 9,486,633 B2 | 11/2016 | Kramer et al. | |
| 9,533,149 B2 | 1/2017 | Lee et al. | |
| 9,561,371 B2 | 2/2017 | Elborno | |
| 9,630,011 B2 | 4/2017 | Lipani | |
| 9,757,584 B2 | 9/2017 | Burnett et al. | |
| 9,782,589 B2 | 10/2017 | Oron et al. | |
| 9,789,313 B2 | 10/2017 | Lipani | |
| 9,833,614 B1* | 12/2017 | Gliner | A61N 1/36139 |
| 9,861,547 B2 | 1/2018 | Crunick et al. | |
| 9,884,189 B2 | 2/2018 | Boggs, II | |
| 9,895,530 B2 | 2/2018 | Boggs, II | |
| 9,895,539 B1 | 2/2018 | Heit | |
| 9,950,164 B2 | 4/2018 | Lipani | |
| 10,143,850 B2 | 12/2018 | Cowan et al. | |
| 10,307,585 B2 | 1/2019 | Boggs et al. | |
| 10,493,275 B2 | 2/2019 | Alataris | |
| 10,232,180 B2 | 3/2019 | Kramer et al. | |
| 10,238,872 B2 | 3/2019 | Pivonka et al. | |
| 10,328,256 B1* | 6/2019 | Gliner | A61N 1/36139 |
| 10,342,977 B2 | 7/2019 | Raghunathan | |
| 10,369,366 B2 | 8/2019 | Oron et al. | |
| 10,426,959 B2 | 10/2019 | Boggs, II | |
| 10,583,284 B2 | 3/2020 | Peters et al. | |
| 10,668,285 B2 | 6/2020 | Boggs, II | |
| 10,799,701 B2 | 10/2020 | Lee | |
| 2003/0018367 A1* | 1/2003 | DiLorenzo | A61N 1/36007 607/46 |
| 2004/0039425 A1 | 2/2004 | Greenwood-Van Meerveld | |
| 2005/0240241 A1 | 10/2005 | Yun et al. | |
| 2008/0033511 A1* | 2/2008 | Dobak | A61N 1/3605 607/66 |
| 2009/0076565 A1 | 3/2009 | Surwit | |
| 2010/0274314 A1 | 10/2010 | Alataris | |
| 2012/0303098 A1 | 11/2012 | Perryman | |
| 2013/0204324 A1* | 8/2013 | Thacker | A61N 1/36071 607/46 |
| 2014/0316484 A1 | 10/2014 | Edgerton et al. | |
| 2015/0073510 A1 | 3/2015 | Perryman | |
| 2016/0030408 A1 | 2/2016 | Levin | |
| 2016/0121109 A1 | 5/2016 | Edgerton | |
| 2016/0177298 A1 | 6/2016 | Green | |
| 2017/0095667 A1 | 4/2017 | Yakovlev | |
| 2017/0274212 A1 | 9/2017 | Kramer et al. | |
| 2017/0354831 A1 | 12/2017 | Burnett et al. | |
| 2018/0028824 A1 | 2/2018 | Pivonka et al. | |
| 2018/0085580 A1* | 3/2018 | Perez | A61N 1/0492 |
| 2018/0256906 A1 | 9/2018 | Pivonka et al. | |
| 2018/0272132 A1* | 9/2018 | Subbaroyan | A61N 1/36171 |
| 2018/0318585 A1 | 11/2018 | Pfeifer | |
| 2018/0345020 A1 | 12/2018 | Ironi et al. | |
| 2018/0361154 A1 | 12/2018 | Levin | |
| 2019/0001139 A1 | 1/2019 | Mishra et al. | |
| 2019/0151652 A1 | 5/2019 | Boggs, II | |
| 2019/0232062 A1 | 8/2019 | Falowski | |
| 2019/0269913 A1 | 9/2019 | Pivonka et al. | |
| 2019/0321641 A1* | 10/2019 | Baldoni | A61N 1/36189 |
| 2019/0336776 A1 | 11/2019 | Cowan et al. | |
| 2019/0351235 A1 | 11/2019 | Leuthardt et al. | |
| 2019/0374776 A1 | 12/2019 | Mishra et al. | |
| 2020/0030606 A1 | 1/2020 | Boggs, II | |
| 2020/0046981 A1 | 2/2020 | Kramer et al. | |
| 2020/0108251 A1 | 4/2020 | Raghunathan | |
| 2020/0139138 A1 | 5/2020 | Sit et al. | |
| 2020/0324113 A1 | 10/2020 | Fisher | |
| 2020/0353253 A1 | 11/2020 | Subbaroyan et al. | |

FOREIGN PATENT DOCUMENTS

| | | |
|---|---|---|
| WO | WO-2017142948 | 8/2017 |
| WO | WO-2017146658 | 8/2017 |
| WO | WO-2020051484 | 3/2020 |

OTHER PUBLICATIONS

Daousi C et al., "Electrical spinal cord stimulation in the long-term treatment of chronic painful diabetic neuropathy" Diabet Med. 2005;22(4):6 pages.

De Vos et al., "Burst spinal cord stimulation evaluated in patients with failed back surgery syndrome and painful diabetic neuropathy" Neuromodulation. 2014;17(2): 8 pages.

De Vos et al., Effect and safety of spinal cord stimulation for treatment of chronic pain caused by diabetic neuropathy. J Diabetes Complications. 2009;23(1): 6 pages.

De Vos et al., "Spinal cord stimulation in patients with painful diabetic neuropathy: a multicentre randomized clinical trial," Pain. 2014;155(11):.6 pages.

Duarte et al., "Quality of life increases in patients with painful diabetic neuropathy following treatment with spinal cord stimulation" Qual Life Res. 2016;25(7):7 pages.

Eisenberg et al., "Quantitative Sensory Testing for Spinal Cord Stimulation in Patients With Chronic Neuropathic Pain. Pain Practice" 2006;6(3):5 pages.

Eldabe et al. "Retrospective Case Series on the Treatment of Painful Diabetic Peripheral Neuropathy With Dorsal Root Ganglion Stimulation." Neuromodulation. 2018;21(8): 6 pages.

Koetsier et al., "Effectiveness of dorsal root ganglion stimulation and dorsal column spinal cord stimulation in a model of experimental painful diabetic polyneuropathy," CNS Neurosci Ther. 2019:25(3): 8 pages.

Koetsier et al., "Mechanism of dorsal root ganglion stimulation for pain relief in painful diabetic polyneuropathy is not dependent on GABA release in the dorsal horn of the spinal cord" CNS Neurosci Ther. 2020;26(1): 8 pages.

Kumar et al., "Spinal cord stimulation for chronic pain in peripheral neuropathy" Surg Neurol. 1996;46(4):7 pages.

Pluijms et al. "Increased contact heat evoked potential stimulation latencies in responders to spinal cord stimulation for painful diabetic polyneuropathy," Neuromodulation. 2015;18(2) 7 pages.

Pluijms et al., "Pain relief and quality-of-life improvement after spinal cord stimulation in painful diabetic polyneuropathy: a pilot study" British Journal of Anaesthesia. 2012;109(4):7 pages.

Pluijms et al., "The effect of spinal cord stimulation frequency in experimental painful diabetic polyneuropathy" Eur J Pain. 2013;17(9):9 pages.

Slangen et al., "Spinal cord stimulation and pain relief in painful diabetic peripheral neuropathy: a prospective two-center randomized controlled trial" Diabetes Care. 2014;37(11): 9 pages.

Van Beek et al. "Sustained Treatment Effect of Spinal Cord Stimulation in Painful Diabetic Peripheral Neuropathy: 24-Month Follow-up of a Prospective Two-Center Randomized Controlled Trial. Diabetes Care" 2015;38(9):3 pages.

Van Beek et al., "Long-Term Spinal Cord Stimulation Alleviates Mechanical Hypersensitivity and Increases Peripheral Cutaneous Blood Perfusion in Experimental Painful Diabetic Polyneuropathy" Neuromodulation. 2018;21(5):8 pages.

Van Beek et al., "Severity of Neuropathy Is Associated With Long-term Spinal Cord Stimulation Outcome in Painful Diabetic Peripheral Neuropathy: Five-Year Follow-up of a Prospective Two-Center Clinical Trial" Diabetes Care. 2018;41(1): 7 pages.

International Search Report and Written Opinion for International Patent Application No. PCT/US2019/024860, Applicant: Nevro Corp., dated Aug. 8, 2019, 14 pages.

(56) References Cited

OTHER PUBLICATIONS

Al-Kaisy et al., "The Use of 10-Kilohertz Spinal Cord Stimulation in Cohort of Patients with Chronic Neuropathic Limb Pain Refractory to Medical Management," Neuromodulation: Technology at the Neural Interface, Feb. 2014, 7 pages.
Tesfaye et al., "Electrical Spinal-Cord Stimulation for Painful Diabetic Peripheral Neuropathy," The Lancet, vol. 348, Dec. 1996, 4 pages.
Van Beek et al., "Spinal Cord Stimulation in Experimental Chronic Painful Diabetic Polyneuropathy: Delayed Effect of High-Frequency Stimulation," European Journal of Pain, Oct. 2016, 9 pages.
Seattle Pain Relief Now Helping Diabetic Neuropathy Patients Restore Sensation with Spinal Cord Stimulation, PRWeb Online Visibility from Vocus, https://www.prweb.com/releases/diabetic-neuopathy/seattle-tacoma-wa/prweb13080906.htm, 2015, 2 pages.
European Extended Search Report and Written Opinion for European Patent Application No. 19777482.1, Applicant: Nevro Corp, dated Nov. 25, 2021, 8 pages.
Cata et al., "Spinal cord stimulation relieves chemotherapy-induced pain: A Clinical Case Report," Journal of Pain and Symptom Management—10.1016/j.jpainsymman, vol. 27, No. 1, Jan. 2004, 7 pages.
CISION PRWeb, "Seattle Pain Relief Now Offering Groundbreaking Treatments for Diabetic and Peripheral Neuropathy," http://www.prweb.com/releases/seattle-pain-center/diabeticneuropathydoctor/prweb12492970.htm Jul. 25, 2022, 3 pages.
McDonnell et al., "Treatment of pain secondary to diabetic peripheral neuropathy (DPN) wit the precisions spinal cord stimulation (SCS) system: a case series," European Journal of Pain 11(S1), 2007, 1 page.
National Institute of Neurological Disorders and Stroke (NINDS), "Paresthesia," https://www.ninds.gov/Disorders/All-Disorders/Paresthesia-Information-Page#disorders-r3>, 2014, 2 pages.
Seattle Pain Relief Video: "What is a Spinal Cord Stimulator," https://www.painmanagementseattle.com/spinal-cord-stimulator.html 2016, 5 pages.
YouTube Video: Spinal Cord Stimulator Implants Help Diabetic Peripheral Neuropathy (602) 507-6550, https://www.youtube.com/watch?v=EYao-SfPOwo, Jul. 23, 2012, 3 pages.

\* cited by examiner

THERAPEUTIC MODULATION TO TREAT BLOOD GLUCOSE ABNORMALITIES, INCLUDING TYPE 2 DIABETES, AND/OR REDUCE HBA1C LEVELS, AND ASSOCIATED SYSTEMS AND METHODS

CROSS-REFERENCE TO RELATED APPLICATION

The present application is a continuation of U.S. patent application Ser. No. 16/369,814, file Mar. 29, 2019, which claims priority to U.S. Provisional Patent Application No. 62/649,838, filed on Mar. 29, 2018 and incorporated herein by reference.

TECHNICAL FIELD

The present technology is directed generally to methods and systems for treating treat blood glucose abnormalities, including metabolic syndrome, type 2 diabetes (T2D), and/ or elevated HbA1c levels in a patient by applying electrical stimulation to a target neural population located within the patient's spinal cord.

BACKGROUND

Neurological stimulators have been developed to treat various medical conditions including pain, movement disorders, functional disorders, spasticity, cancer, and cardiac disorders, amongst other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

While the foregoing stimulators and treatments have proven beneficial in many instances, there remains a significant need in the medical community for improved therapies that can address metabolic diseases, such as diabetes and more particularly, type 2 diabetes (T2D).

DETAILED DESCRIPTION

Figure 1A:
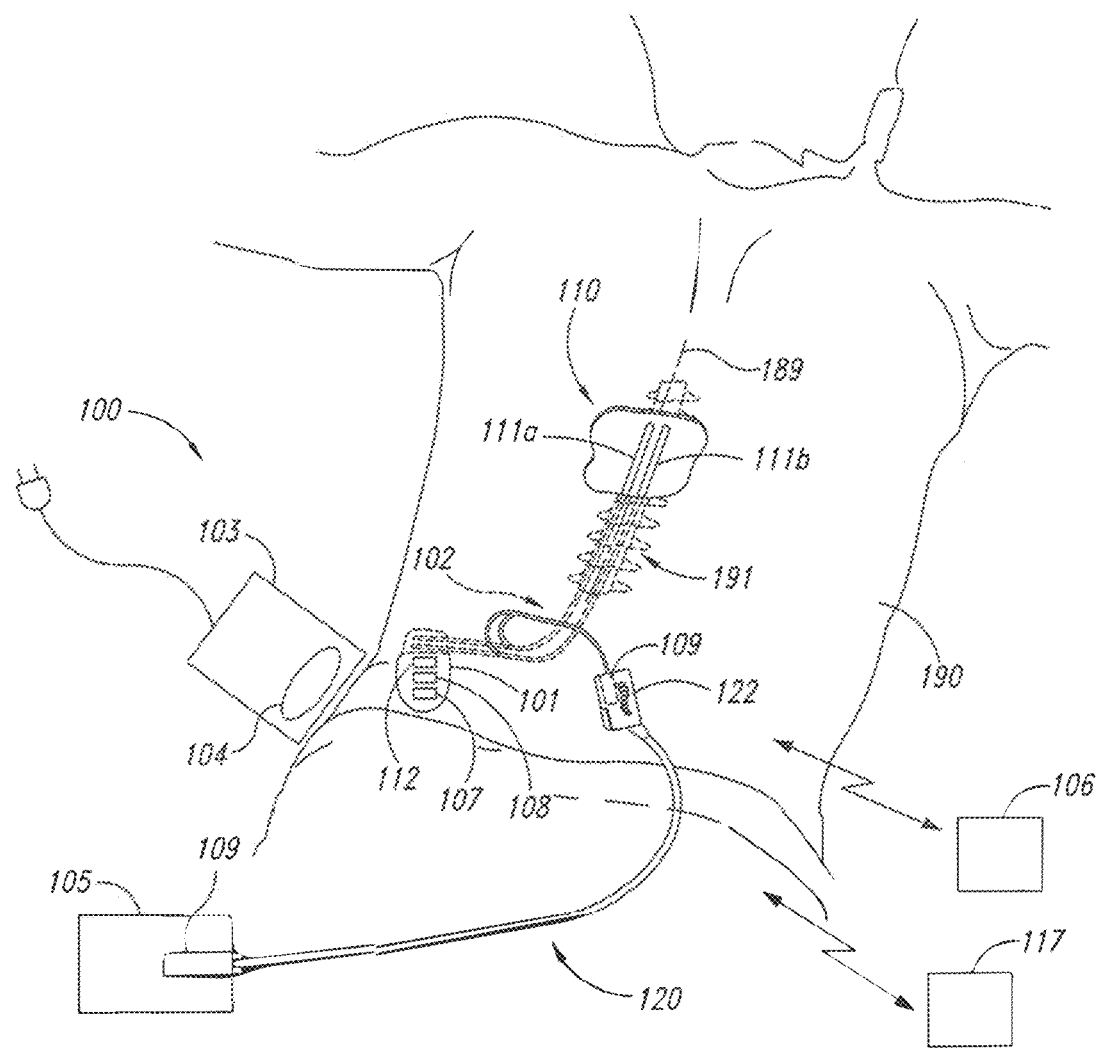
FIG. 1A is a partially schematic illustration of an implantable spinal cord modulation system positioned at a patient's spine to deliver therapeutic signals in accordance with representative systems and methods of the present technology.

Definitions of selected terms are provided under Heading 1.0 ("Definitions"). General aspects of the anatomical and physiological environment in which the disclosed technology operates are described below under Heading 2.0 ("Introduction"). Representative treatment systems and their characteristics are described under Heading 3.0 ("System Characteristics") with reference to FIGS. 1A and 1B. Representative methods for treating blood glucose abnormalities via the representative systems, and target locations for positioning leads are described under Heading 4.0 ("Representative Methods for Treating Blood glucose abnormalities") with reference to FIGS. 2A-7. Representative examples are described under Heading 5.0 ("Representative Examples").

1.0 Definitions

As used herein, the term "electrical signal" refers generally to an electrical signal that may be characterized by one or more parameters, for example, frequency, pulse width, and/or amplitude. Representative electrical signals disclosed herein can have (1) a frequency of from about 1.2 kHz to about 100 kHz, or to about 50 kHz, or to about 25 kHz, or to about 10 kHz, or from about 1.5 kHz to about 100 kHz, or from about 2 kHz to about 50 kHz, or from about 3 kHz to about 20 kHz, or from about 3 kHz to about 15 kHz, or from about 5 kHz to about 15 kHz, or from about 3 kHz to about 10 kHz, or 1 kHz, 2 kHz, 3 kHz, 4 kHz, 5 kHz, 10 kHz, 15 kHz, 20 kHz, 25 kHz, 50 kHz, or 100 kHz; (2) an amplitude within an amplitude range of about 0.1 mA to about 20 mA, about 0.5 mA to about 10 mA, about 0.5 mA to about 7 mA, about 0.5 mA to about 5 mA, about 0.5 mA to about 4 mA, about 0.5 mA to about 2.5 mA; (3) a pulse width in a pulse width range of from about 1 microsecond or less to about 416 microseconds, from about 10 microseconds to about 333 microseconds, from about 10 microseconds to about 166 microseconds, from about 25 microseconds to about 166 microseconds, from about 25 microseconds to about 100 microseconds, from about 30 microseconds to about 100 microseconds, from about 33 microseconds to about 100 microseconds, from about 50 microseconds to about 166 microseconds; and/or (4) a zero or non-zero interphase delay, including a 20 microsecond interphase delay between a 30 microsecond cathodic pulse and a following 30 microsecond anodic pulse, followed by another 20 microsecond interphase.

As used herein, a "program" refers generally to one or more electrical signal parameters that can be used to characterize the electrical signal. A program can accordingly include a signal frequency, pulse width, amplitude, duty cycle, electrical contacts to which the signal is directed, time of day at which the signal is active, and/or other suitable parameters. A given device can be programmed with one or more programs that can be activated (e.g., simultaneously or sequentially), or deactivated.

Unless otherwise stated, the terms "about" and "approximately" refer to values within 10% of a stated value.

As used herein, the term "blood glucose abnormalities" refers generally to abnormalities in the ways the patient's body handles/responds to glucose, including but not limited to higher than normal HbA1c levels, higher than normal fasting blood glucose levels, higher than normal oral glucose tolerance tests, and/or a state of persistent hyperglycemia, often associated with metabolic syndrome.

As used herein, "type II diabetes (T2D)" refers generally to a disease of impaired glucose metabolism and/or impaired insulin-dependent regulation of glucose levels. While T2D is systemic, it affects the liver, pancreas, kidneys, stomach, adrenal glands, heart, blood vessels, nerves, eyes, feet, hands, skin, and brain more so than other organs. The systems and methods of the present technology are configured to treat T2D. For the purposes of this description T2D is a blood glucose abnormality.

The term "metabolic syndrome" generally refers to a clustering of at least three of the five following medical conditions: central obesity, high blood pressure, high blood sugar, high serum triglycerides, and low serum high-density lipoprotein. Metabolic syndrome increases the risk of developing T2D, and these patients can be pre-diabetic or have T2D. Insulin resistance, metabolic syndrome, and prediabetes are closely related to one another. The syndrome is thought to be caused by an underlying disorder of energy utilization and storage, and therapies aimed at T2D often are efficacious in patients with metabolic syndrome. For the purposes of this description metabolic syndrome is also considered a blood glucose abnormality.

"Treating" or "treatment" as used herein refers generally to preventing progression and/or onset of blood glucose abnormalities, including T2D and/or metabolic syndrome, ameliorating, reducing, eliminating, suppressing, and/or alleviating blood glucose abnormalities, and/or one or more of the symptoms associated with blood glucose abnormalities, generating a complete or partial regression of blood glucose abnormalities, or any suitable combination thereof. "Treatment" also refers to reducing a patient's HbA1c levels.

As used herein, and unless otherwise noted, the terms "modulate," "modulation," "stimulate," and "stimulation" refer generally to signals that have any of the foregoing effects. Accordingly, a spinal cord "stimulator" can have an inhibitory or excitatory effect on certain neural populations.

As used herein, the term "HbA1c" refers generally to hemoglobin A1c, a glycated form of hemoglobin.

The following terms are used interchangeably throughout the present disclosure: electrical signal, electrical stimulation, therapeutic modulation signal, therapy signal, therapeutic signal, electrical pulse, signal, waveform, modulation signal, modulation, neural modulation signal, and therapeutic electrical signal.

"Representative systems" and "representative methods" are described below as including one or more features. The representative systems and methods can, but need not necessarily, include those features.

2.0 Introduction

The present technology is directed generally to spinal cord modulation and associated systems and methods for treating blood glucose abnormalities, including metabolic syndrome, type 2 diabetes (T2D), and/or reducing HbA1c levels via waveforms with therapeutic electrical signal elements or components that provide therapeutic results. While representative systems and methods are described below in the context of T2D, such systems and methods may also address the overarching blood glucose abnormality, and/or other patient indications associated with the blood glucose abnormality. The systems and methods described herein may treat a blood glucose abnormality generally without generating paresthesia, which may or may not be a side effect, depending, for example, on the particular patient. Additional side effects can include unwanted motor stimulation or blocking, and/or interference with sensory functions other than the targeted blood glucose abnormality. Representative systems and methods continue to provide therapy for blood glucose abnormalities, and/or reduction of HbA1c levels for at least some period of time after the modulation signals have ceased. Although some representative systems and methods are described below with reference to modulating the dorsal column, dorsal horn, dorsal root, dorsal root entry zone, and other particular regions of the spinal column to treat the blood glucose abnormality, the modulation may, in some instances be generally directed to the patient's thoracic region (e.g., T2-T12) of the spinal column, and/or other neurological structures and/or target neural populations of other neurological tissues, organs, and/or tissues. In at least some representative systems and methods, therapy signals delivered at thoracic vertebral levels within the forgoing range may affect the splenic nerve, which branches from the spinal cord at multiple vertebral levels.

Specific details of representative systems and methods of the present technology are described below with reference to methods for modulating one or more target neural populations within the patient's spinal cord and/or other sites of a patient, and associated implantable structures for providing the modulation. Some representative systems and methods can have configurations, components and/or procedures different than those which are described herein, and others may eliminate particular components or procedures. A person of ordinary skill in the relevant art, therefore, will understand that the present disclosure may include representative systems and methods with additional elements, and/or may include representative systems and methods without several of the features shown and described below with reference to FIGS. 1A-8.

Also provided herein are representative neuromodulation systems, methods, and therapies for treating blood glucose abnormalities (including T2D) and/or reducing HbA1c levels. Unless otherwise specified, the representative systems and methods discussed are not to be construed as limitations on the scope of the disclosed technology. It will be apparent to one skilled in the relevant art that various equivalents, changes, and modifications may be made without departing from the scope of the disclosed technology, and it is understood that such equivalent systems and methods are to be included herein.

In general terms, the present technology is directed to producing a therapeutic effect that includes reducing or eliminating the blood glucose abnormality and/or one or more symptoms thereof in the patient. Other effects (e.g., associated with blood glucose abnormalities) that can be reduced or eliminated include symptoms such as high blood pressure, excess body fat around the waist, and/or abnormal cholesterol or triglyceride levels. The therapeutic effect can be produced by inhibiting, suppressing, downregulating, blocking, preventing, and/or otherwise modulating the activity of the affected and/or target neural population, such as a target neural population in the thoracic region of the patient's spinal column (e.g., T2-T12). In representative systems and methods, the affected neural population is located within, proximate to, or otherwise corresponds to the patient's sympathetic nervous system, which modulates glycogen production and regulates the patient's production and/or response to insulin. Without intending to be bound by any particular theory, inhibiting at least a portion of the patient's sympathetic nervous system, such as one or more sympathetic nerves corresponding to one or more of the patient's liver, adrenal gland(s), pancreas, kidney(s), or gastrointestinal system (stomach, large intestine, and/or small intestine), may result in the therapeutic effect by increasing glycogen production (e.g., hepatic glycogenesis), increasing insulin sensitivity, increasing the patient's gastrointestinal contraction rate which, without intending to be bound by any particular theory, may induce release of glucagon-like peptide-1 (GLP-1) from the patient's intestine, and/or otherwise altering insulin production and/or glucose storage (e.g., in the form of glycogen). In representative systems and methods, the therapeutic effect may be produced by inhibiting one or more sympathetic nerves corresponding to one or more thoracic vertebrae in the range of T2 to T12.

The techniques described below with reference to FIGS. 1A-8 can produce more effective, more robust, less complicated and/or otherwise more desirable results than can existing stimulation therapies and/or other T2D therapies. In particular, these techniques can produce results that reduce or eliminate the blood glucose abnormality and/or persist after the modulation signal ceases. These techniques can be performed by delivering modulation signals continuously or intermittently (e.g., on a schedule) to obtain a beneficial effect with respect to treating the blood glucose abnormality.

Many of the following representative systems and methods produce a therapeutic effect that includes treating the blood glucose abnormality in a patient. The therapeutic effect can be produced by inhibiting, suppressing, downregulating, blocking, preventing, and/or otherwise modulating the activity of the affected neural population.

In representative systems and methods, therapeutic modulation signals are directed to the target location that generally includes the patient's spinal cord, e.g., the dorsal column of the patient's spinal cord. The modulation signals can be directed to the dorsal horn, dorsal root, dorsal root ganglion, dorsal root entry zone, and/or other particular areas at or in close proximity to the spinal cord itself. The foregoing areas are referred to herein collectively as the spinal cord region. In representative systems and methods, therapeutic modulation signals are directed generally to lamina X of the patient's spinal cord via (1) conduction of the patient's cerebral spinal fluid at the patient's dorsal median sulcus, (2) one or more of laminae I-IX, or (3) both. In still further examples, the modulation signals may be directed to other neurological structures and/or target neural populations.

Without being bound by the following theories, or any other theories, the therapy signals may act to treat the blood glucose abnormality via one or both of two mechanisms: (1) by reducing neural transmissions entering the sympathetic nervous system, and/or (2) by reducing neural activity at the sympathetic nerves themselves. The presently disclosed therapy can treat the blood glucose abnormality, in some cases, accompanied by paresthesia, and in other cases, without the sensory effects (e.g., paresthesia) and/or other effects generally associated with conventional SCS therapies e.g., including but not limited to, SCS therapies conducted below 1200 Hz. Several representative SCS therapies that include stimulation at frequencies above 1.5 kHz are discussed further in U.S. Pat. No. 8,170,675, incorporated herein by reference. These and other advantages associated with the presently disclosed technology are described further below.

3.0 System Characteristics

Representative systems include a signal generator (or pulse generator) that is implantable or external. The signal generator is coupleable to an implantable signal delivery device that directs electrical signals to target neural populations of the patient. Representative systems can include other elements as well, for example, one or more devices to program or update the signal delivery parameters in accordance with which the electrical signals are delivered to the patient.

Representative systems direct electrical signals from electrical contacts, (positioned at selected locations relative to the patient's anatomy), to target neural populations, in accordance with further signal delivery parameters. Representative signal delivery parameters include:

Example 1

Stimulation location: T9-T10; frequency: 10 kHz; pulse width: 30 microseconds; amplitude; 0.5-5 mA.

Example 2

Stimulation location: C8-T12; frequency: 1.2-100 kHz; pulse width: 1-416 microseconds; amplitude; 0.5-15 mA.

Example 3

Stimulation location: T2-T12; frequency: 1.2-50 kHz; pulse width: 10-416 microseconds; amplitude; 0.5-10 mA.

Example 4

Stimulation location: T2-T10; frequency: 1.2-25 kHz; pulse width: 20-416 microseconds; amplitude; 0.5-7.5 mA.

Example 5

Stimulation location: T4-T8; frequency: 5-25 kHz; pulse width: 20-100 microseconds; amplitude; 1-7.5 mA.

The representative systems described under Heading 3.0 and elsewhere herein can be used to carry out the methods described later under Heading 4.0 and elsewhere herein.

FIG. 1A schematically illustrates a representative patient therapy system 100 for treating a patient's blood glucose abnormalities (e.g., T2D or metabolic syndrome), arranged relative to the general anatomy of the patient's spinal column 191. The system 100 can include a signal generator 101 (e.g., an implanted or implantable pulse generator or IPG), which may be implanted subcutaneously within a patient 190 and coupled to one or more signal delivery elements or devices 110. The system 100 can also include an external pulse generator, described in further detail later. The signal delivery elements or devices 110 may be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102 and/or a wireless link. In representative systems, the signal delivery devices 110 can include one or more elongated lead(s) or lead body or bodies 111 (identified individually as a first lead 111a and a second lead 111b). As used herein, the terms signal delivery device, lead, and/or lead body include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In representative systems and methods, the signal delivery elements 110 can include structures other than a lead body (e.g., a paddle, having an array of disc-shaped electrodes facing toward the target tissue) that also direct electrical signals and/or other types of signals to the patient 190, e.g., as disclosed in U.S. Patent Publication No. 2018/0256892, which is incorporated herein by reference in its entirety.

In representative systems and methods, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. In representative methods, the leads 111 may be implanted at a vertebral level ranging from, for example, about T2 to about T12. In representative methods, one or more signal delivery devices can be implanted at other vertebral levels.

The signal generator 101 can transmit signals (e.g., electrical signals) to the signal delivery elements 110 that excite and/or suppress target nerves (e.g., sympathetic nerves). The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components. Further, the pulse generator 101 and/or other system components can include dedicated hardware, firmware, and/or software for executing computer-executable instructions that, when executed, perform any one or more methods, processes, and/or sub-processes described in the materials incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety. Specific details regarding sensors that detect patient-specific levels of compounds specifically associated with Type 2 diabetes are described below with reference to FIG. 8, along with feedback techniques to control the therapy based on the detected levels and/or other relevant physiological characteristics.

In representative systems and methods, the signal generator 101 and/or signal delivery devices 110 can obtain power to generate the therapy signals from an external power source 103. For example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In representative systems and methods, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator (e.g., an external pulse generator) 105 can be coupled to the signal delivery elements 110 during an initial procedure, prior to implanting the signal generator 101, or the external pulse generator can be used for chronic therapy. For example, a practitioner (e.g., a physician and/or a company representative) can use the external stimulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In representative systems and methods, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120.

After the signal delivery elements 110 are implanted, the patient 190 can (optionally) undergo a trial period during which the patient receives therapy via signals generated by the trial modulator 105, generally for a limited period of time. During this time, the patient wears the cable assembly 120 and the trial modulator 105 outside the body. Based on the outcome of the trial, the practitioner may replace the trial modulator 105 with the implanted signal generator 101, and program the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use. In some instances, the trial period can be eliminated, and the patient can proceed directly to an implanted pulse generator, and fully implanted signal delivery device. Furthermore, in representative systems and methods, external stimulator can be linked with the implanted signal delivery device(s) via a wireless link, rather than a cable assembly, for transmitting power, electrical signals, and/or data to the signal delivery device(s), on a temporary basis (e.g., during the trial period), and/or chronically.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, which is incorporated by reference herein in its entirety.

In representative systems and methods, the present technology includes receiving patient feedback, via a sensor and/or other input device that is indicative of, or otherwise corresponds to, the patient's response to the signal. Feedback includes, but is not limited to, physiological feedback (e.g., motor and/or sensory feedback, detected levels of selected compounds in the blood, blood pressure, and/or other patient state measures), and verbal feedback. In response to the patient feedback, one or more signal parameters can be adjusted, such as frequency, pulse width, amplitude or delivery location. Further details are described later with reference to FIG. 8.

Figure 1B:
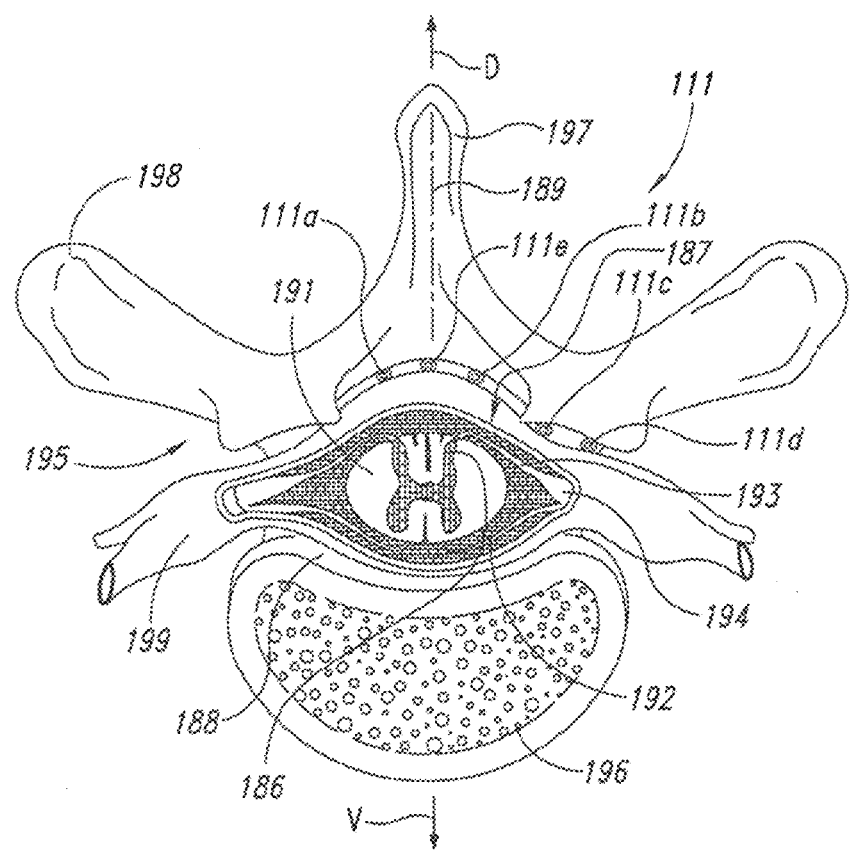
FIG. 1B is a partially schematic, cross-sectional illustration of a patient's spine, illustrating representative locations for implanted lead bodies in accordance with representative systems and methods of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated, generally cylindrical leads with corresponding cylindrical contacts, however, the leads 111 can be paddle leads, e.g., having a generally flattened, planar substrate with disc-shaped electrodes facing toward the target tissue. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In representative systems and methods, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In representative systems and methods, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e. The lead can be positioned epidurally to deliver electrical therapy signals to target neural populations in the spinal cord region, including the spinal cord itself.

Representative systems and methods can include other features. For example, one lead 111 to six leads 111 can be positioned generally end-to-end at or near the patient's midline M and span vertebral levels from about T2 to about T12. In some instances, two, three, or four leads 111 are positioned end-to-end at or near the patient's midline from T2 to T12. Without intending to be bound by any particular theory, positioning one or more leads 111 at the patient's midline M can mimic bilateral autonomic and pain effects of therapy observed with patients receiving electrical therapy signals to address diabetic neuropathy, chronic abdominal pain, and other types of pain and/or autonomic dysfunction. In addition, the devices and systems of the present technology can include more than one internal stimulator and/or more than one external stimulator that can be configured for wireless stimulation, such as by using electromagnetic waves.

Several aspects of the technology are embodied in computing devices, e.g., programmed/programmable pulse generators, controllers and/or other devices. The computing devices on/in which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In representative systems, the computer readable media are tangible media. In representative systems, the data structures and message structures may be stored or transmitted via an intangible data transmission medium, such as a signal on a communications link. Various suitable communications links may be used, including but not limited to a local area network and/or a wide-area network.

In representative systems and methods, it is important that the signal delivery device 110 and in particular, the therapy or electrical contacts of the device, be placed at or proximate to a target location that is selected (e.g., by a practitioner) to produce efficacious results in the patient when the device 110 is activated. Section 4.0 describes techniques and systems for positioning leads 111 in the patient's spinal column to deliver neural modulation signals to treat the patient's blood glucose abnormality.

4.0 Representative Methods for Treating Blood Glucose Abnormalities

The representative systems described above under Heading 3.0 and elsewhere herein can be used to carry out the methods described under Heading 4.0 and elsewhere herein.

The autonomic nervous system (ANS) is largely responsible for automatically and subconsciously regulating many systems of the body, including the cardiovascular, renal, gastrointestinal, and thermoregulatory systems. By regulating these systems, the ANS can enable the body to adapt to changes in the environment. Autonomic nerve fibers innervate a variety of tissues, including cardiac muscle, smooth muscle, and glands. These nerve fibers help to regulate functions associated with the foregoing tissues, including but not limited to blood pressure, blood flow, gastrointestinal functions, body temperature, bronchial dilation, blood glucose levels and/or storage, blood insulin levels and/or storage, insulin production and/or metabolism, glycogen levels and/or storage, glycogen production and/or metabolism, HbA1c levels and/or storage, HbA1c production and/or metabolism, metabolism, micturition and defecation, pupillary light and accommodation reflexes, adrenal hormone, GLP-1, and glandular secretions. The autonomic nervous system includes the sympathetic system and the parasympathetic system. These two systems in many instances have opposite effects and accordingly, each one can balance the effect of the other. Additional features of the ANS and application of therapeutic modulation signals to modulate a patient's ANS are described in U.S. Pat. No. 9,833,614, incorporated by reference herein in its entirety.

Without intending to be bound by any particular theory, T2D may be caused, at least in part, by increased effects of the patient's sympathetic system. One approach to treating T2D and/or reducing HbA1c levels in accordance with representative systems and methods of the present technology is to apply therapeutic signals to inhibit one or more effects of the patient's sympathetic system. One possible mechanism of action by which therapeutic signals may treat the blood glucose abnormality is to reduce the excitability of wide dynamic range (WDR) neurons. Accordingly, therapeutic signals directed to treating blood glucose abnormalities (including T2D and/or metabolic syndrome) can operate in a manner similar and/or analogous to that associated with pain treatment to inhibit at least a portion of the patient's sympathetic system. The effect of therapeutic modulation signals on WDR neurons is described in U.S. Pat. No. 9,833,614, previously incorporated by reference herein in its entirety.

Therapeutic modulation at or near one or more of the patient's thoracic vertebrae T2 to T12, and in particular at T9 and/or T10, as well as T5 and/or T6, can treat the patient's blood glucose abnormality, without paresthesia, without adverse sensory or motor effects, and/or in a manner that persists after the modulation ceases. T5/T6 generally corresponds to the liver, stomach, and pancreas and T9/T10 generally corresponds to the adrenals and intestines. Therapeutic modulation at or near one or more of the patient's thoracic vertebrae T2 to T12 can improve glucose intolerance and insulin resistance by any of a number of different mechanisms.

Because anatomies can vary from one patient to another, some patients may receive effective therapy at vertebral levels above or cephalad to T2 (e.g., C8, C9 and/or T1), simply because the relevant nerves exit the spinal canal at positions different than for the majority of patients. Accordingly, the present technology, and any representative systems and methods described in the context of electrical signals applied to vertebral levels from T2-T12, can be applied at vertebral levels from C9-T12 so as to include such patients.

Without intending to be bound by any particular theory, delivering therapeutic modulation signals may improve glucose tolerance in patients having blood glucose abnormalities (e.g., T2D and/or metabolic syndrome) by increasing incretin release, e.g., GLP-1 and/or GIP release, in the patient's intestines, and/or reducing ghrelin release in a portion of the patient's gastric system. The present technology provides methods and devices for treating the patient's blood glucose abnormalities (e.g., T2D and/or metabolic syndrome), and/or reducing the patient's HbA1c levels. Methods and systems for treating the patient's blood glucose abnormality by applying therapeutic modulation signals to thoracic neural populations, are discussed immediately below.

Figure 2A:
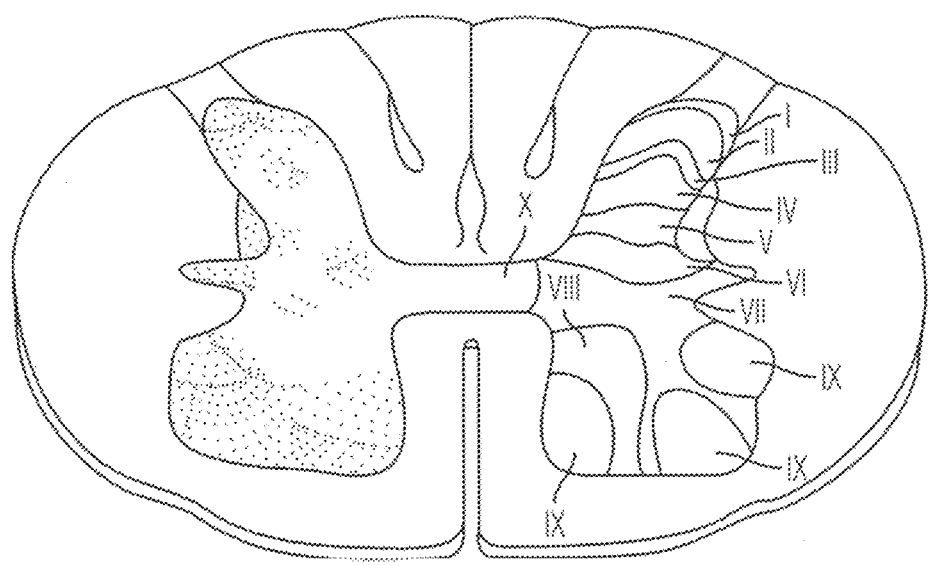
FIG. 2A is partially schematic cross-sectional illustration of a rat's spinal cord illustrating laminae that may be targeted by therapy signals in accordance with representative systems and methods of the present technology.

FIG. 2A is a partially schematic cross-sectional illustration of a patient's spinal cord 191 showing relative locations of laminae I-X within the spinal cord. As discussed herein, delivering a therapeutic electrical signal to inhibit at least a portion of the patient's sympathetic nervous system, such as a sympathetic nerve, can treat the patient's blood glucose abnormality. In representative systems and methods, the therapeutic electrical signal is delivered to the portion of the patient's sympathetic nerves by an implanted signal delivery device, such as those described herein. More specifically, and without intending to be bound by any particular theory, the inhibitory effects of the therapeutic electrical signal can modulate the patient's sympathetic interneurons, which are GABAergic and elicit monosynaptic inhibitory post synaptic potentials in sympathetic preganglionic neurons (SPNs) within the intermediolateral cell column. Sympathetic interneurons are generally located in laminae V, VII, and X of the patient's spinal cord and less often in superficial laminae I-IV.

Without intending to be bound by any particular theory, deeper laminae, such as lamina V-X and in particular lamina X, may be associated with sympathetic modulation by mediating any inhibitory effects of the therapeutic modulation signal on one or more of the patient's sympathetic nerves. In representative systems and methods, the therapeutic electrical signal is directed to lamina X of the patient's spinal cord to inhibit the patient's sympathetic system, such as via the sympathetic interneurons. These inhibitory effects of the therapeutic modulation signal can promote glycemic control in patients with T2D, such as by promoting glucose uptake by the patient's liver.

Figure 2B:
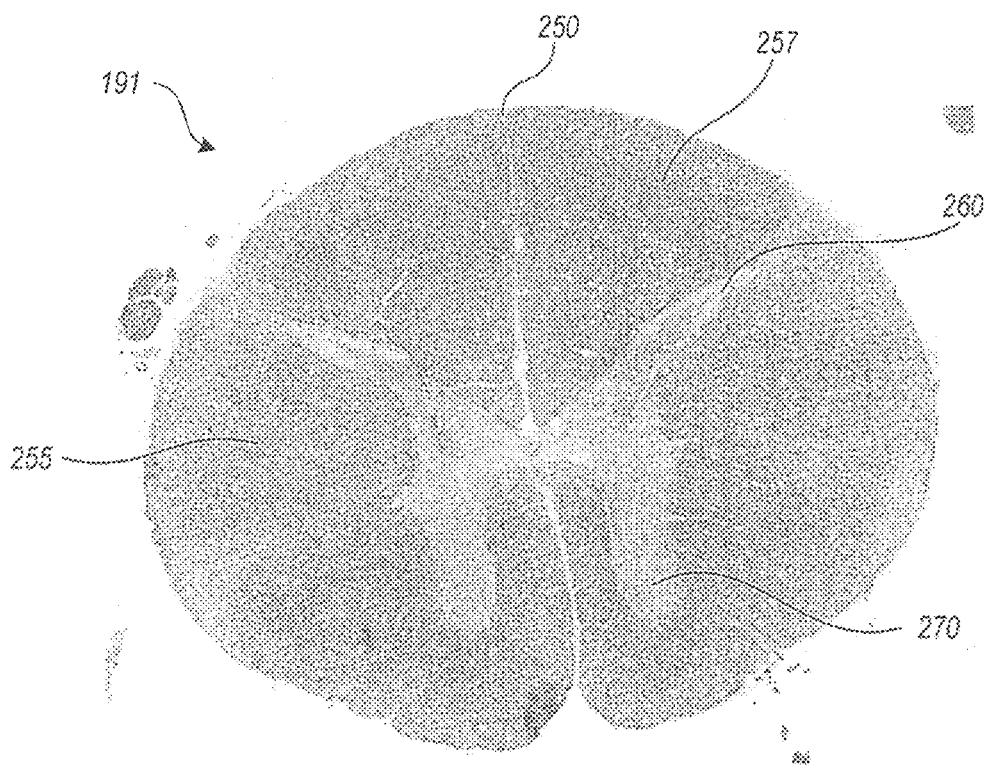
FIG. 2B is cross-sectional image of a patient's thoracic spinal cord illustrating structures that may be targeted by therapy signals in accordance with representative systems and methods of the present technology.

FIG. 2B is a histological image of a rat thoracic spinal cord. As shown in FIG. 2B, the dorsal median sulcus 250 separates the patient's left dorsal column 255 and right dorsal column 257. The dorsal median sulcus 250 contains cerebral spinal fluid, which is about five times more conductive than the white or gray matter of the patient's spinal column. The therapeutic electrical signal may reach lamina X of the patient's spinal cord (1) via conduction of the patient's cerebral spinal fluid at the patient's dorsal median sulcus, (2) via one or more of laminae I-IX, (3) via another mechanism, or (4) a combination of any of (1)-(3). The dorsal horn 260 and the ventral horn 270 are shown for purposes of orientation.

Figure 3:
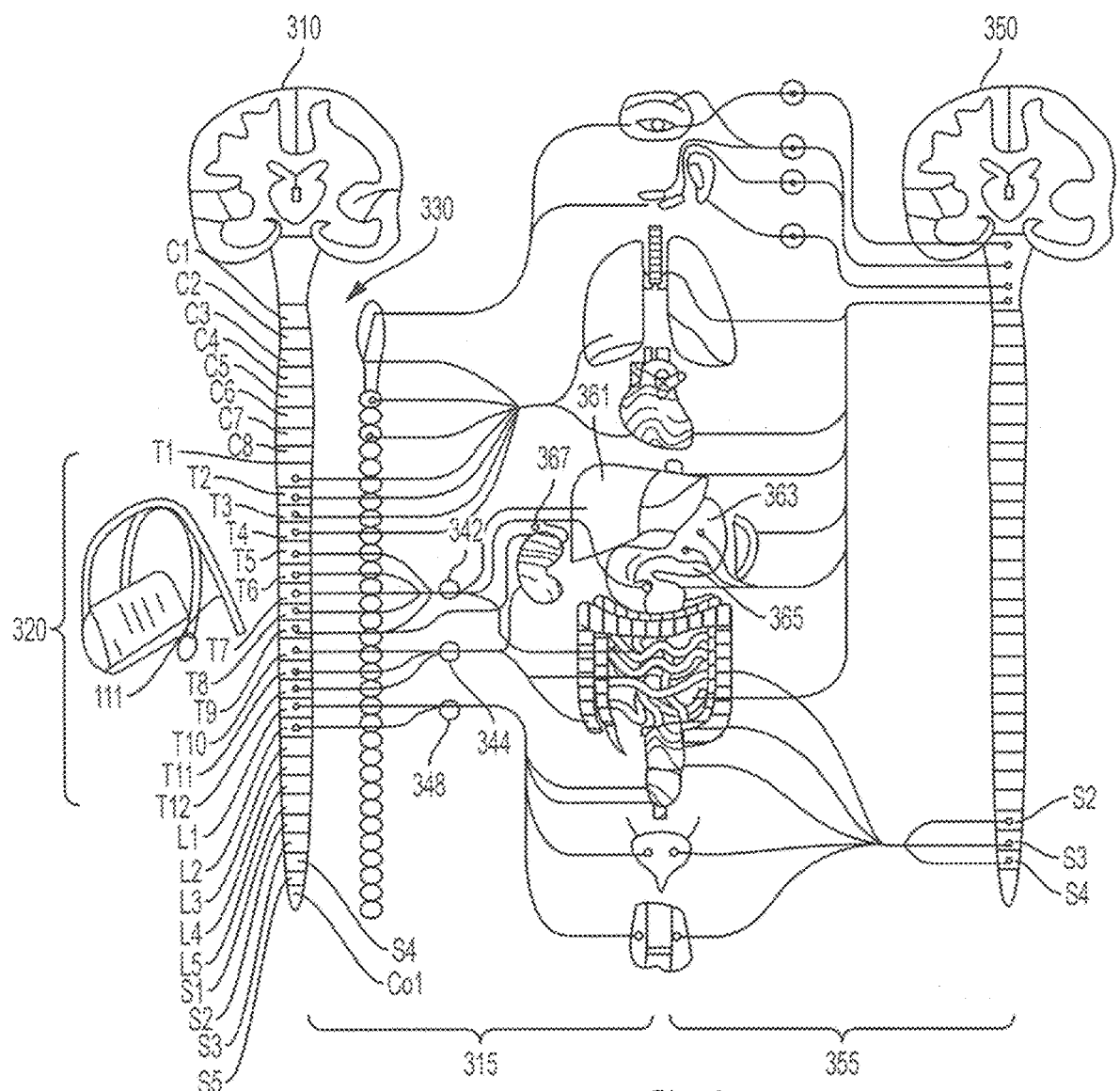
FIG. 3 is a partially schematic illustration of a patient's sympathetic and parasympathetic nervous systems, and some of the organs innervated thereby, and also illustrating a representative location for an implanted lead body in accordance with representative systems and methods of the present technology.

FIG. 3 is a partially schematic illustration of a patient's sympathetic nervous system 310 and parasympathetic nervous system 350, and the organs innervated by the corresponding sympathetic nerves 315 and/or the parasympathetic nerves 355. A lead body 111 (shown prior to implant in FIG. 3) can be positioned at or proximate to the thoracic region 320 (e.g., T1-T12) of the patient's spinal column 330. Applying a therapeutic modulation signal to a target location at or between T2 to T12 of the patient's thoracic region may modulate one or more of the patient's sympathetic nerves 315, such as the celiac ganglia 342, the superior mesenteric ganglia 344, and the inferior mesenteric ganglia 348. In representative systems and methods, the modulation inhibits one or more of the sympathetic nerves 315 innervating the patient's liver 361, pancreas 365, adrenal gland 367, and/or stomach 363. By inhibiting one or more of the sympathetic nerves 315, glucose uptake by the patient's liver 361 may increase, which lowers the patient's post-prandial blood glucose levels, thereby treating the patient's T2D.

Figure 4A:
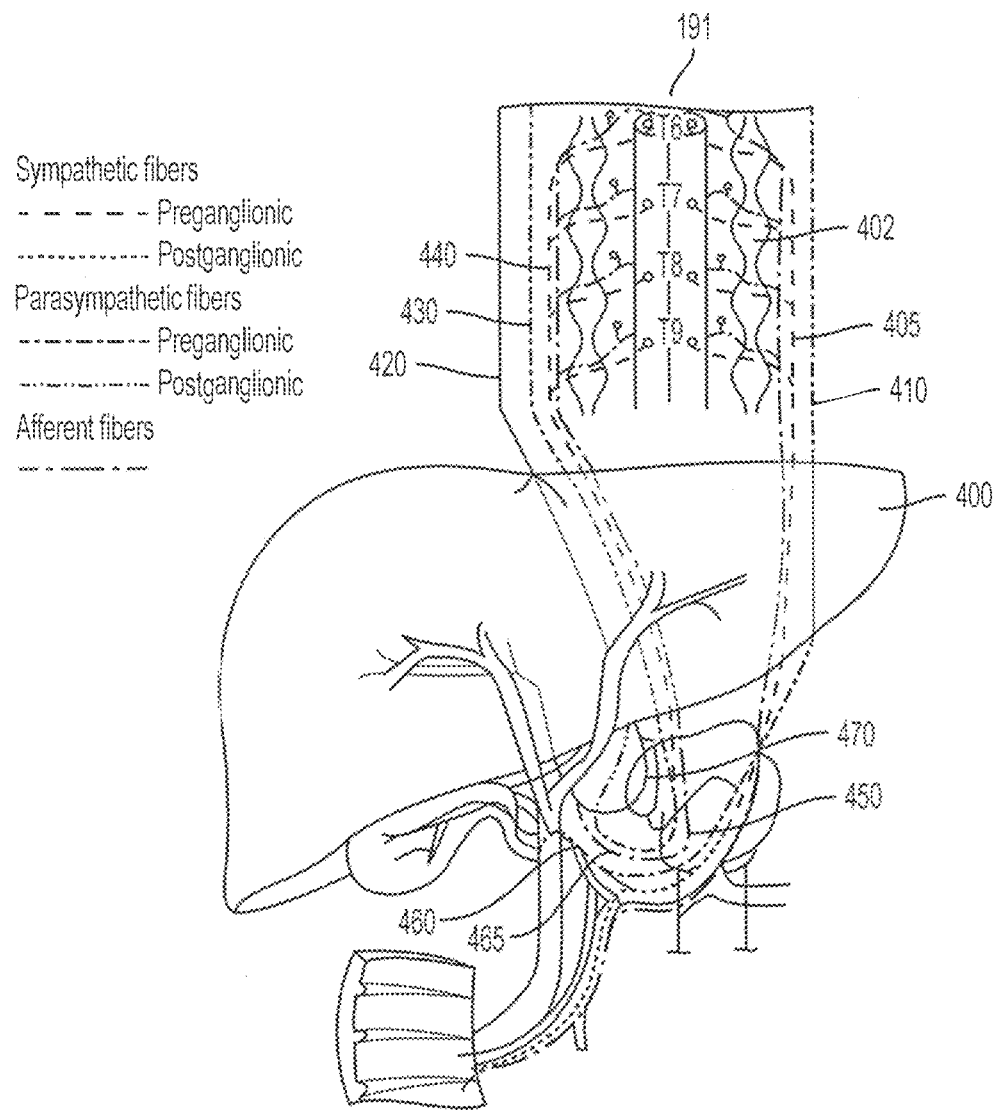
FIG. 4A is a partially schematic illustration of a patient's spinal cord and an enlarged illustration of the patient's liver, illustrating sympathetic nerves innervating the liver, which may be affected by representative systems and methods of the present technology.

FIG. 4A is a partially schematic illustration of a patient's spinal cord 191 and an enlarged illustration of the patient's liver 400, illustrating sympathetic nerves innervating the liver 400. The sympathetic chain ganglion 402 is shown for reference. Nerves which innervate the liver extend from the left greater thoracic splanchnic nerve 405, the anterior vagal trunk 410, the right phrenic nerve 420, the posterior vagal trunk 430, and the right greater thoracic splanchnic nerve 440. In addition, the anterior hepatic plexus 460, the posterior hepatic plexus 465, and the phrenic ganglion 470 also extend into the liver 400. The celiac ganglion 450 is also shown for reference. Delivering the therapeutic signals of the present technology can exert a therapeutic benefit upon the liver 400. In representative systems and methods, the therapeutic signals will decrease the sympathetic tone innervating the liver, which will increase post-prandial uptake of glucose in the liver that is stored as glycogen. In representative systems and methods, the therapeutic signals exert these benefits by affecting metabolism of insulin, glucagon, GLP-1, and/or the adrenal hormone. In representative systems and methods, the therapeutic signals can also directly affect the patient's liver 400, such as by inducing one or more effects of insulin, glucagon, GLP-1, and/or the adrenal hormone on the patient's liver 400. The therapeutic signals can affect a ratio of insulin and glucagon, and these ratios may be pathologic in a patient having T2D. For example, the ratio of insulin to glucagon may be too high in a hyperinsulinemic T2D patient. In representative systems and methods, therapeutic signals can lower a patient's need for insulin which can induce release of glucagon from the patient's liver 400, such as by reducing insulin levels.

Figure 4B:
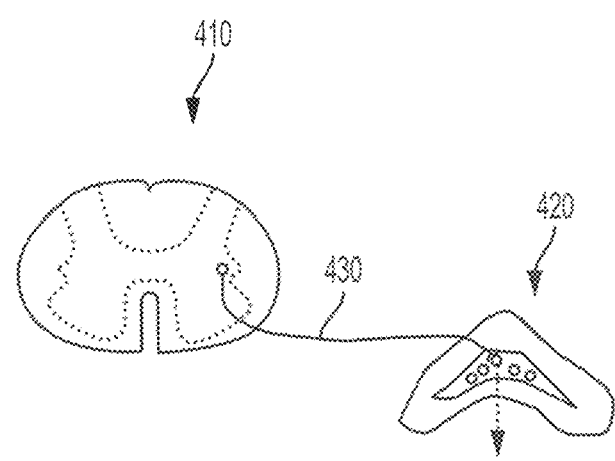
FIG. 4B is a partially schematic cross-sectional illustration of a patient's spinal cord and an enlarged illustration of the patient's adrenal medulla, illustrating a sympathetic preganglionic neuron (SPN) innervating the adrenal medulla, which may be affected by representative systems and methods of the present technology.

FIG. 4B is a partially schematic cross-sectional illustration of a patient's spinal cord 410, and an enlarged illustration of the patient's adrenal medulla 420. The adrenal medulla 420 is directly innervated by sympathetic preganglionic neurons (SPNs) 430. The SPNs 430 promote release of catecholamines (dotted arrow) which are associated with increased blood glucose levels, by promoting glucose release from the patient's liver. Delivering one or more therapeutic modulation signals to one or more of the patient's sympathetic interneurons in lamina X can directly and/or indirectly inhibit SPN activity which can indirectly affect glucose metabolism in the patient's liver, e.g., as described above with reference to FIG. 4A.

Figure 5:
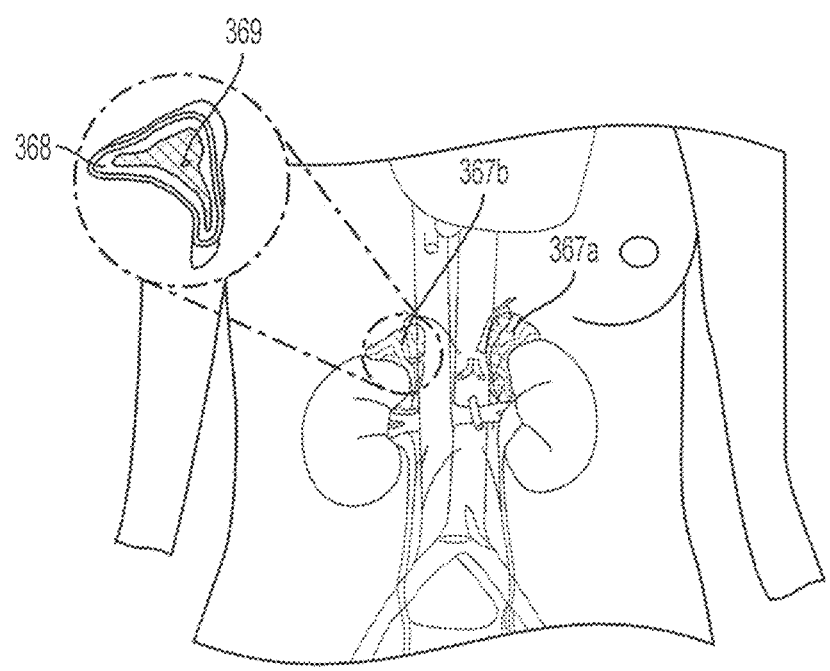
FIG. 5 is a partially schematic illustration of a portion of a patient's renal system, including an enlarged illustration of the adrenal gland which may be targeted by therapy signals in accordance with representative systems and methods of the present technology.

FIG. 5 is a partially schematic illustration of a portion of a patient's renal system. In particular, FIG. 5 shows the patient's adrenal glands 367a and 367b, each of which includes an adrenal cortex 368 and an adrenal medulla 369. As shown in FIG. 5, the patient's left adrenal gland 367a is proximally located from the patient's right adrenal gland 367b. In representative systems and methods, the implantable stimulation devices (e.g., leads 111) can be placed at different levels relative to the patient's spinal column and in some cases, on opposite sides of the patient's spinal column. For example, to inhibit the sympathetic nerves innervating the left adrenal gland 367a, a first lead can be positioned proximate to and on the right side of the patient's T10 vertebra whereas, to inhibit the sympathetic nerves innervating the right adrenal gland 367b, a second lead can be positioned proximate to and on the left side of the patient's T9 vertebra. As another example, the first lead can be positioned proximate to and on the left side of the patient's T10 vertebra and the second lead can be positioned proximate to and on the right side of the patient's T9 vertebra. The vertebral locations are not limited to T9 and T10 and can also include any number of thoracic vertebrae from T2 to T12.

Figure 6:
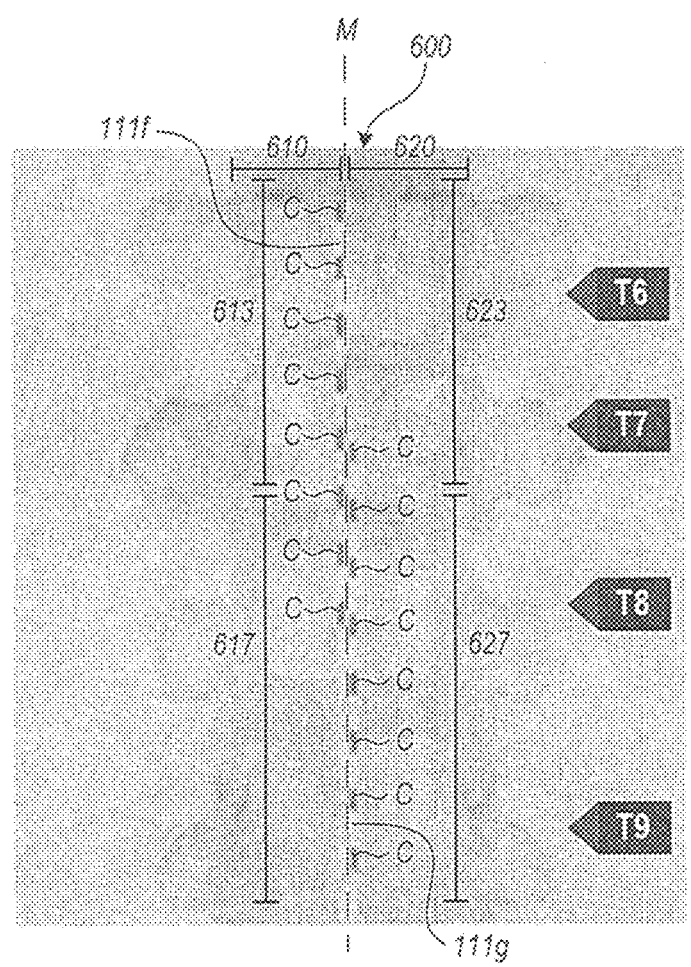
FIG. 6 is an image of a patient's spine illustrating representative locations of implanted lead bodies in accordance with representative systems and methods of the present technology.

FIG. 6 is an image of a patient's spine 600 along with two percutaneous signal delivery devices 111 (shown as signal delivery devices 111f and 111g) implanted at representative locations. For purposes of illustration, two signal delivery devices 111 are shown in FIG. 6 implanted in the same patient. In actual use, any given patient may receive more or less than the two signal delivery devices 111g and 111f shown in FIG. 6.

As illustrated in FIG. 6, a first signal delivery device 111f having a first plurality of contacts C is positioned on a first side 610 of a midline M of the patient's spinal column 600 and a second implantable signal delivery device 111g having a second plurality of contacts C is positioned on a second side 620 of the midline M. The first plurality of contacts C are positioned longitudinally along the first side 610 of the midline M, from T8 to T10, and the second plurality of contacts are positioned longitudinally along the second side 620 of the midline M, from T9 to T11. In representative systems and methods, the first implantable signal delivery device 111f and the second implantable signal delivery device 111g can be positioned on the same side of the midline M (e.g., either the first side 610 or the second side 620). In representative systems and methods, the first plurality of contacts C can be positioned longitudinally along the first side 610 of the midline M, from T7 to T10, and the second plurality of contacts are positioned longitudinally along the second side 620 of the midline M, from T5 to T8. In representative systems and methods, the vertebral ranges in which the first plurality of contacts C and the second plurality of contacts C can differ from those disclosed herein.

As illustrated in FIG. 6, the first implantable signal delivery device 111f and the second implantable signal delivery device 111g are shown overlapping by about ½ to about ⅓ of a length of each of the signal delivery devices. However, in representative systems and methods the first implantable signal delivery device 111f and the second implantable signal delivery device 111g do not overlap. For example, the second implantable signal delivery device 111g can be positioned at least generally end to end such that the first plurality of contacts C and the second plurality of contacts C extend generally longitudinally along the midline M.

In representative systems and methods, the first implantable signal delivery device 111f can also be positioned to span a first portion 613 of the patient's tissue on a first side 610 of the midline M and a first portion 623 of the patient's tissue on a second side 620 of the midline M. The second implantable signal delivery device 111g can be positioned to span a second portion 617 of the patient's tissue on the first side 610 of the midline and a second portion 627 of the patient's tissue on the second side 620 of the midline M. When positioned to span the first side 610 and the second side 620 of the midline M, at least one contact C of the first plurality of contacts is positioned proximate to the first portion 613 of the first side 610 and at least one contact C of the first plurality of contacts is positioned proximate to the first portion 623 of the second side 620. In addition, at least one contact C of the second plurality of contacts is positioned proximate to the second portion 617 of the first side 610 and at least one contact C of the second plurality of contacts is positioned proximate to the second portion 627 of the second side 620.

The therapeutic electrical stimulation signals can be delivered to a target location. In representative systems and methods, the target location can also include a first target portion and a second target portion. For example, the first implanted signal delivery device 111f can be positioned proximate to the first target portion 623 and/or the second implanted signal delivery device 111g can be positioned proximate to the second target portion 627. In representative systems and methods, the first target portion is proximate to a first thoracic vertebrae and the second target portion is proximate to a second thoracic vertebrae that can be the same or different from the first thoracic vertebrae.

After positioning, the therapeutic modulation signal can be delivered to the patient's target location at generally the same time (e.g., simultaneously or approximately simultaneously) via one or more implantable therapeutic signal delivery devices. In general, inhibiting the sympathetic nerves to treat the blood glucose abnormality may be achieved following delivery of one or more therapeutic modulation signals having one or more stimulation parameters at or proximate to one or more of T2 to T12 vertebrae, e.g., T9 and/or T10. For example, the stimulation parameters include, but are not limited to, amplitude, frequency, pulse width, duty cycling, and whether stimulation is applied at or proximate to the patient's left side or the patient's right side of their midline.

In a representative system and method, the therapeutic modulation signal has an amplitude from about 20% to about 90% of the patient's sensory threshold, a frequency of about 10 kHz, and a pulse width of about 30 microseconds, but representative systems and methods can have any one of the amplitudes, frequencies and/or pulse widths disclosed throughout this disclosure and particularly under Headings 3.0 and 4.0. As described elsewhere herein, the therapeutic modulation signal can be delivered to the patient pre-prandially, prandially, and/or post-prandially and in representative systems and methods, one or more stimulation parameters of the therapeutic modulation signal can differ between a pre-prandial therapeutic modulation signal, prandial therapeutic modulation signal, and/or post-prandial therapeutic modulation signal. For purposes of the present technology, prandial refers to the duration of time when the patient is consuming calories, and the prandial time period can, in accordance with representative systems and methods, range from about 30 minutes to about 120 minutes.

In representative systems and methods, one or more therapeutic modulation signals can be delivered to a target location proximate to at one or more vertebral levels in the range of C8-T12, T2-T12, T4-T10, or T4 to T6. At least at T4-T6, the therapeutic modulation signals may inhibit at least a portion of the patient's celiac ganglion associated with sympathetic nerves that innervate the patient's stomach, liver, pancreas, and/or adrenal glands. Inhibiting the patient's sympathetic nerves associated with one or more of the target locations at or proximate to T4 to T6 can be achieved by positioning one or more implantable therapeutic signal delivery devices at or proximate to one or more of T4 to T6. Inhibiting one or more of the patient's sympathetic nerves can promote glucose uptake in the patient's liver and/or lower the patient's post-prandial blood glucose levels.

In representative systems and methods, one or more therapeutic modulation signals can be delivered to a target location proximate to or at one or more of T7 to T12. These therapeutic modulation signals may inhibit at least a portion of the patient's celiac ganglion and/or superior mesenteric ganglia, associated with sympathetic nerves that innervate the patient's small and large intestine, as well as the patient's stomach, duodenum, jejunum, and ileum. Inhibiting the patient's sympathetic nerves associated with one or more of T7 to T12 can be achieved by positioning at least one (e.g., at least two, in some cases) implantable therapeutic signal delivery devices at or proximate to one or more of T7 to T12. Without intending to be bound by any particular theory, inhibiting one or more of the patient's sympathetic nerves can increase incretin release from the patient's intestine and/or ghrelin release from the patient's stomach.

In representative systems and methods, slow waves (e.g., rhythmic electrophysiological events) of the patient's gastrointestinal region of interest can be normalized by changing the duty cycle of the therapeutic modulation signal, such as by altering one or more of the on cycle portion of the duty cycle and/or the off cycle portion of the duty cycle. In representative examples:

(1) the normal slow wave frequency is about 3 waves per minute, and the electrical signal has an on cycle of about 20 seconds, and an off cycle of about 20 seconds, to inhibit the sympathetic nerves that innervate the patient's stomach, (2) the normal slow wave frequency is about 12 waves per minute, and the electrical signal has an on cycle of about 5 seconds, and an off cycle of about 5 seconds, to inhibit the sympathetic nerves that innervate the patient's duodenum, (3) the normal slow wave frequency is about 11 waves per minute, and the electrical signal has an on cycle of about 5.5 seconds, and an off cycle of about 5.5 seconds, to inhibit the sympathetic nerves that innervate the patient's jejunum, (4) the normal slow wave frequency is about 8 waves per minute, and the electrical signal has an on cycle of about 7.5 seconds, and an off cycle of about 7.5 seconds, to inhibit the sympathetic nerves that innervate the patient's ileum, and (5) the normal slow wave frequency is about 6 waves per minute, and the electrical signal has an on cycle of about 10 seconds, and an off cycle of about 10 seconds, to inhibit the sympathetic nerves that innervate the patient's large intestine.

The efficacy of any of the foregoing duty cycles may be subject to an overarching "wash-in" and/or "wash-out" period of days or weeks, as has been observed in other applications of electrical signals in the frequency range of 1.2 kHz-100 kHz.

In representative systems and methods, the therapeutic signal is delivered to patients continuously or intermittently, such as at various times throughout the day. When delivered intermittently, the therapeutic signal can be coordinated to be pre-prandial, prandial, and post-prandial. For example, the therapeutic signal can be delivered while the patient is prandial and, by doing so, increase the uptake of glucose by the patient's liver, compared to prandial patients not receiving the therapeutic signal. The duration of prandial time can be from about 30 minutes to about 120 minutes, and can differ within a single day or it can be generally the same. In representative systems and methods, the therapeutic signal can be delivered at an amplitude having an amplitude range of between about 20% to about 90% of the patient's sensory threshold, at a frequency of about 10 kHz, and/or about a 30 microsecond pulse width.

Figure 7:
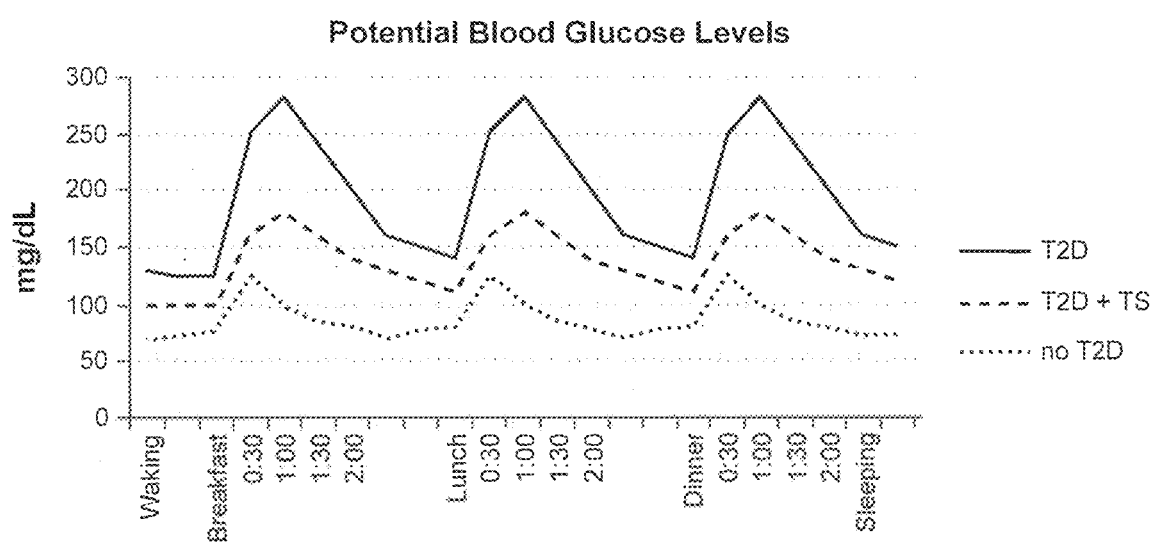
FIG. 7 is a chart illustrating a potential effect of therapeutic electrical therapy on blood glucose levels occurring between waking and sleeping in accordance with representative systems and methods of the present technology.

FIG. 7 illustrates expected blood glucose levels of (1) a patient who has T2D and is not receiving any therapeutic modulation signals, (2) a patient who has T2D and is receiving one or more therapeutic modulation signals described herein (e.g., electrical stimulation therapy), and (3) a patient who does not have T2D. As shown in FIG. 7, each patient's blood glucose levels rise from pre-prandial levels while the patient is prandial (e.g., eating breakfast, lunch, and/or dinner) and fall while the patient is post-prandial (e.g., after the patient has stopped eating). In representative systems and methods, the electrical stimulation therapy is delivered intermittently to treat the patient's T2D, such as intermittently during one or more of the pre-prandial, peri-prandial (e.g. at or near the prandial phase), prandial, post-prandial, and sleeping phases. Without intending to be bound by any particular theory delivering one or more of the therapeutic modulation signals described herein to a patient having T2D can decrease the T2D patient's pre-prandial, prandial, and post-prandial blood glucose levels compared to the T2D patient not receiving the therapy.

In representative systems and methods, the electrical signal is delivered during the peri-prandial phase and the prandial phase can be the same as the therapy delivered during a non-prandial phase (e.g., pre-prandial, post-prandial, and/or sleeping phase). For example, the electrical signal delivered during the peri-prandial phase and/or the prandial phase can include 2 to 5 bipoles, such as 3 to 4 bipoles and the therapy delivered during non-prandial phases can include one or more pulses. Without intending to be bound by any particular theory, stimulating multiple bipoles simultaneously at multiple spinal levels can provide a broader sympathetic inhibition to various organs involved in diabetes, including the liver, stomach, pancreas, adrenals, and intestines. Further, delivering the pulses on an intermittent basis can promote motility within the patient's digestive system and preserve battery power. In representative systems and methods, the electrical signal delivered during the sleeping phase can also differ from the electrical signal delivered during other phases. For example, certain electrical signals can avoid certain phenomenon effects in some patients, e.g., Somogyi effects and dawn phenomenon effects. These effects can involve hypoglycemic or near hypoglycemic events between about 1:00 am and 4:00 am, such as between about 2:00 am and about 3:00 am, that initiate a hyperglycemic sympathetic response once the patient wakes, e.g., in the morning. In representative systems and methods, electrical signals delivered during the sleeping phase include an off period between about 1:00 am and about 4:00 am to prevent the hyperglycemic sympathetic response from occurring.

In representative systems and methods, the therapeutic modulation signals can be generally synchronized for delivery when the patient is prandial and for a duration of time while the patient is post-prandial. For example, the T2D patient can receive one or more therapeutic modulation signals when his/her prandial phase begins, and the one or more therapeutic modulation signals can be continuously or intermittently delivered to the T2D patient for about 30 minutes to about 120 minutes during the prandial phase and/or extending into the post-prandial phase. Delivering one or more therapeutic modulation signals described herein to a patient having T2D can maintain the T2D patient's blood glucose levels between about 75 mg/dL and about 200 mg/dL, and more specifically, between about 100 mg/dL and about 175 mg/dL. For example, the therapeutic modulation signal(s) can reduce the T2D patient's blood glucose level by at least about 10%, at least about 15%, at least about 20%, at least about 25%, at least about 30%, at least about 35%, at least about 40%, at least about 45%, or at least about 50% following delivery of the therapeutic modulation signal (e.g., electrical therapy signal).

In representative systems and methods, the T2D patient's HbA1c levels can also be altered following delivery of or more therapeutic modulation signals. For example, the T2D patient's HbA1c level is reduced by at least about 1%, at least about 1.5%, at least about 2%, at least about 2.5%, at least about 3%, at least about 3.5%, at least about 4%, at least about 4.5%, at least about 5%, at least about 6%, at least about 7%, at least about 8%, at least about 9%, or at least about 10% following delivery of the electrical signal.

While representative systems and methods of the present technology may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with T2D) can be maintained at pre-treatment levels. For example, the patient can experience a significant reduction in T2D, HbA1c levels, and/or one or more associated symptoms, largely independent of the patient's movement and position. In particular, the patient can assume a variety of positions, consume various amounts of food and liquid, and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to undergo T2D treatment (or treatment for corresponding symptoms) while engaging in a variety of activities. This result can also provide an improved lifestyle for patients who experience symptoms associated with T2D during sleep.

In representative systems and methods, patients can choose from a number of signal delivery programs (e.g., two, three, four, five, or six), each with a different amplitude and/or other signal delivery parameter, to treat the patient's blood glucose abnormality. In representative systems and methods, the patient can activate one program before sleeping and another after waking, or the patient can activate one program before sleeping, a second program after waking, and a third program before engaging in particular activities that would otherwise trigger, enhance, or otherwise exacerbate the patient's blood glucose abnormality, such as pre-prandial, prandial, and/or post-prandial activities. In representative systems and methods, the patient can activate a fourth program when the patient is pre-prandial, a fifth program when the patient is prandial, and/or a sixth program when the patient is post-prandial. In representative systems and methods, the fourth program and/or the sixth program can be the same, and can also be generally the same as the programs activated before sleeping and/or after waking. This reduced set of patient options can greatly simplify the patient's ability to easily manage the blood glucose abnormality, without reducing (and in fact, increasing) the circumstances under which the therapy effectively addresses the blood glucose abnormality. In representative systems and methods which include multiple programs, the patient's workload can be further reduced by automatically detecting a change in patient circumstance, and automatically identifying and delivering the appropriate therapy regimen. Additional details of such techniques and associated systems are disclosed in U.S. Pat. No. 8,355,797, incorporated herein by reference.

In representative systems and methods, rather than the patient activating one or more programs, the systems, devices, and methods described herein automatically detect a beginning and/or an end of one or more prandial events. For example, the systems, devices, and methods described herein can automatically detect one or more prandial events by monitoring the patient's blood glucose levels, either intermittently or continuously and if a change in the patient's blood glucose level is detected, the systems, devices, and methods described herein can automatically deliver therapeutic electrical signals. Representative systems and methods described herein can include one or more sensors configured to monitor the patient's blood glucose levels by detecting an amount of glucose in the patient's blood.

In representative systems and methods, electrical stimulation may be administered on a pre-determined schedule or on an as-needed basis. Administration may continue for a pre-determined amount of time, or it may continue indefinitely until a specific therapeutic benchmark is reached, for example until an acceptable reduction in one or more symptoms is obtained. In representative systems and methods, electrical stimulation may be administered one or more times per day, one or more times per week, once a week, once a month, or once every several months. Since electrical stimulation is thought to improve the patient's blood glucose abnormality (e.g., normalize the patient's blood glucose levels) over time with repeated use of therapeutic electrical signals, the patient may need less frequent electrical signal therapy. In representative systems and methods, the therapy can be delivered when the patient's blood glucose abnormality recurs or increases in severity. Administration frequency may also change over the course of treatment. For example, a patient may receive less frequent administrations over the course of treatment as certain therapeutic benchmarks are met. The duration of each administration (e.g., the actual time during which a subject is receiving electrical stimulation) can remain constant throughout the course of treatment, or it can vary depending on factors such as patient health, internal pathophysiological measures, or symptom severity. In representative systems and methods, the duration of each administration may range from 1 to 4 hours, 4 to 12 hours, 12 to 24 hours, 1 day to 4 days, or 4 days or greater.

As described above, a therapeutic modulation signal in accordance with representative systems and methods can have an amplitude in an amplitude range of between about 20% to about 90% of the patient's sensory threshold, at a frequency of about 10 kHz, and/or about a 30 microsecond pulse width and can be applied at a particular vertebral level associated with the organ of interest, such as at the thoracic vertebral levels (e.g., T2-T12) to inhibit activity of the patient's sympathetic nervous system (e.g., the sympathetic nerves innervating) or otherwise associated with the patient's stomach, liver, pancreas, one or more adrenal glands, duodenum, jejunum, ileum, and large intestine. Further details of particular vertebral levels and associated organs are described herein and in U.S. Pat. No. 8,170,675, previously incorporated herein by reference. In representative systems and methods, additional simulation parameters can be applied to one or more of these vertebral levels to treat the blood glucose abnormality, such as those described below.

In representative systems and methods, therapeutic electrical stimulation to treat a patient's blood glucose abnormality is performed with at least a portion of the therapy signal at a frequency in a frequency range between about 1.2 kHz and about 100 kHz; between about 1.5 kHz and about 100 kHz, between about 1.5 kHz and about 50 kHz; between about 3 kHz and about 20 kHz; between about 3 kHz and about 15 kHz; or between about 5 kHz and about 15 kHz; or at frequencies of about 5 kHz, about 6 kHz, about 7 kHz, about 8 kHz, about 9 kHz, about 10 kHz, about 11 kHz, about 12 kHz, about 10 kHz, about 25 kHz, or about 50 kHz.

In representative systems and methods, therapeutic electrical stimulation to treat a patient's blood glucose abnormality is performed with at least a portion of the therapy signal at amplitudes within amplitude ranges of: about 0.1 mA to about 20 mA; about 0.5 mA to about 10 mA; about 0.5 mA to about 7 mA; about 0.5 mA to about 5 mA; about 0.5 mA to about 4 mA; and/or about 0.5 mA to about 2.5 mA.

In representative systems and methods, therapeutic electrical stimulation to treat a patient's blood glucose abnormality is performed with at least a portion of the therapy signal having a pulse width in a pulse width range of from about 1 microsecond or less to about 416 microseconds, from about 10 microseconds to about 333 microseconds; from about 10 microseconds to about 166 microseconds; from about 25 microseconds to about 166 microseconds;

from about 25 microseconds to about 100 microseconds; from about 30 microseconds to about 100 microseconds; from about 33 microseconds to about 100 microseconds; from about 30 microseconds to about 40 microseconds, and/or from about 50 microseconds to about 166 microseconds.

In representative systems and methods, therapeutic electrical stimulation to treat a patient's blood glucose abnormality is performed with at least a portion of the therapy signal having a 30 microsecond cathodic pulse followed by a 20 microsecond interphase delay followed by a 30 microsecond anodic pulse followed by another 20 microsecond interphase delay. The total phase time duration of 100 microseconds corresponds to a frequency of 10 kHz. The total phase time duration may range from 10-833 microseconds corresponding to frequencies ranging from 1200 Hz-100 kHz. In representative systems and methods, the interphase delays may differ from 20 microseconds and may range from 0 to the maximum difference between the phase time duration and the combined pulse widths of an anodic and cathodic pulse (for a bi-phasic waveform). In representative systems and methods, the cathodic and/or anodic pulses may differ from 30 microseconds and may range from one microsecond or less to the maximum difference between the phase time duration and the duration of an interphase delay (for a bi-phasic waveform). The opposing phases of a given pulse pair may not be symmetric (e.g., may have different widths and/or amplitudes), but generally provide the same magnitude of charge, though at opposite polarities, to provide charge balancing on a pulse-by-pulse basis.

Aspects of the therapy provided to the patient may be varied, while still obtaining beneficial results. For example, the location of the lead body (and in particular, the lead body electrodes or contacts) can be varied throughout and/or across the target location(s) described above, such as target locations proximate to or at T2 to T12, and/or other organs, tissues, and/or neurological structures. Other characteristics of the applied signal can also be varied. In representative systems and methods, the amplitude of the applied signal can be ramped up and/or down and/or the amplitude can be increased or set at an initial level to establish a therapeutic effect, and then reduced to a lower level to save power without forsaking efficacy, as is disclosed in U.S. Patent Publication No. 2009/0204173, incorporated herein by reference. The signal amplitude may refer to the electrical current level, e.g., for current-controlled systems or to the electrical voltage level, e.g., for voltage-controlled systems. The specific values selected for the foregoing parameters may vary from patient to patient and/or from indication to indication and/or on the basis of the selected electrical stimulation location. In addition, the present technology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In representative systems and methods, the parameters in accordance with which the pulse generator provides signals can be modulated during portions of the therapy regimen. For example, the frequency, amplitude, pulse width and/or signal delivery location can be modulated in accordance with a preset program, patient and/or physician inputs, and/or in a random or pseudorandom manner. Such parameter variations can be used to address a number of potential clinical situations, including changes in the patient's perception of one or more symptoms associated with the condition being treated, changes in the preferred target neural population, and/or patient accommodation or habituation.

In representative systems and methods, a practitioner can obtain feedback from the patient to detect the patient's blood glucose levels and/or the effect of the therapeutic modulation signal on the patient's blood glucose abnormality. Monitoring a patient's blood glucose level can be performed on a continuous basis using one or more sensing elements (referred to herein as a "sensing element") for detecting neural signals, neural responses, and/or other physiological parameters of the patient before, during and/or after the application of electrical stimulation signals to the patient. In representative systems and methods, the sensing element can be carried by the signal generator 101, the signal delivery elements 110, and/or other implanted components of the system 100, as previously described with reference to FIG. 1A. As such, the sensing element may be positionable in an area proximate to the target treatment site where electrical stimulation is being delivered. In representative systems and methods, the sensing element can be positioned separate from the signal generator 101 and/or the signal delivery elements 104. For example, the sensing elements may be implanted in an area separate from the area where electrical stimulation is being delivered, or in an extracorporeal manner. When separated from one another, the sensing element and the signal generator 101 may be coupled to one another via a wired link or a wireless link (e.g., via a Bluetooth link).

Representative sensing elements can include an impedance sensor, a chemical sensor, a biosensor, an electrochemical sensor, a hemodynamic sensor, an optical sensor and/or other suitable implantable sensing devices. In representative systems and methods, the sensing element can be a cuff electrode, and can be positioned around a nerve (e.g., the vagus nerve or the splanchnic nerve) or proximate to a target neural population of the patient. The sensing element can detect one or more neural signal(s) and/or neural response(s) (e.g., electrical signals corresponding to action potentials) from the nerve or neural population, and the system (e.g., the system 100 referenced in FIG. 1A) can use the detected neural signal(s) and/or neural response(s) to identify the patient's blood glucose level at a particular moment in time. The neural response(s) can be detected frequently enough such that an upward or downward trend of the data corresponding to the blood glucose levels can be determined, or at least estimated. With regard to glucose in particular, the detected neural response(s) may be associated with the electrical signal that is, for example, generated subsequent to receptors of the neural population binding to glucagon.

The detected neural signal(s) and/or response(s) can include characteristics that may be measured and used to identify the patient's blood glucose levels at a particular point in time. Characteristics can include, for example, signal strength (e.g., whether a value of the signal is above a pre-determined threshold value), frequency (e.g., number of action potentials fired in a given time), amplitude and/or velocity, amongst other measurable characteristics. In representative systems and methods, changes of a characteristic from one or more previous neural signals or neural responses, and/or rates of change of a characteristic from previous neural signals or neural responses, can be used in a similar manner. Measurements associated with the characteristics can then be used to identify blood glucose levels at a particular moment in time. In representative systems and methods, the identified blood glucose levels may be determined or estimated based on a pre-determined correlation between the values of the characteristics of the neural response(s) and the blood glucose levels of the patient or a similarly-situated patient. The correlation may be developed by, for example, controlling a particular glucose concentration of the patient and monitoring neural responses of the patient at that concentration. This process can be repeated for multiple concentrations until a correlation is developed over a range of concentrations.

An advantage of representative systems and methods of the present monitoring technology over conventional or traditional detection methods/devices is that they do not rely on consumable materials that deplete over time. Unlike conventional devices, which need to be replaced after one or more uses, the implantable sensing element of the present technology can determine the patient's blood glucose levels based on characteristics of an electrical signal (i.e., the neural responses of the patient) and thus does not need to be removed and replaced, or at least not as often as devices in accordance with conventional technologies.

Yet another advantage of representative systems and methods of the present monitoring technology over conventional or traditional detection methods/devices is that the accuracy of the present technology does not generally degrade over time. This is unlike conventional devices that include substances and can be used multiple times. Such devices can have issues with accuracy as the devices approach the end of their lifespan.

Monitoring the patient's blood glucose levels, as disclosed herein, can be performed in tandem with modulating electrical therapy signals to the patient. Stated otherwise, the patient's blood glucose levels can be continuously (or periodically) monitored using the methods described herein, and used to determine or adjust the signal delivery parameters so as to improve the effect of the modulated electrical therapy signals. For example, the practitioner can (a) continuously observe/monitor the patient's blood glucose levels to determine a baseline level, (b) direct an electrical therapy signal (e.g., a signal having a frequency from 1.2 kHz to 100 kHz) to a neural population of the patient via an implantable signal delivery device, (c) monitor the patient's blood glucose levels after directing the therapy signal to report changes in diabetic response (e.g., glucose levels, amount of insulin needed, etc.) and/or other functions, and (d) if necessary, adjust the electrical therapy signal to achieve a more desirable blood glucose level. Adjusting the electrical therapy signal can include adjusting one or more signal delivery parameters (e.g., frequency, amplitude, pulse width, duty cycle, and normal slow wave frequency) of the subsequent electrical signal to be applied to the target location. Steps (a)-(d) can be performed iteratively to improve or achieve a desired result for the patient. Suitable methods and products for monitoring this system include those where the patient's response to the electrical stimulation therapy can be adjusted. For example, the patient's response can include one or more measurements of the patient's serum glucose levels, such as an oral glucose tolerance test, fasting blood glucose levels, and HbA1c percentages.

The continuous monitoring methods of the present technology can also be used for applications other than glucose monitoring and T2D. For example, the monitoring methods can be used to monitor other chemicals (e.g., dopamine, serotonin, etc.) based on neural responses of the patient, and to treat other diseases of disorders (e.g., depression, Parkinson's, etc.). Additionally, the monitoring methods of the present technology can be used as a diagnostic tool to pre-emptively monitor diseases. For example, the implantable sensing device can be implanted prior to an onset of any particular disease (e.g., T2D), and data from the sensing device can be used to identify trends that may be used to suggest the onset of the disease. Data from the sensing device can be wirelessly transmitted (e.g., to a server) such that the practitioner can remotely monitor the data and identify trends.

Figure 8:
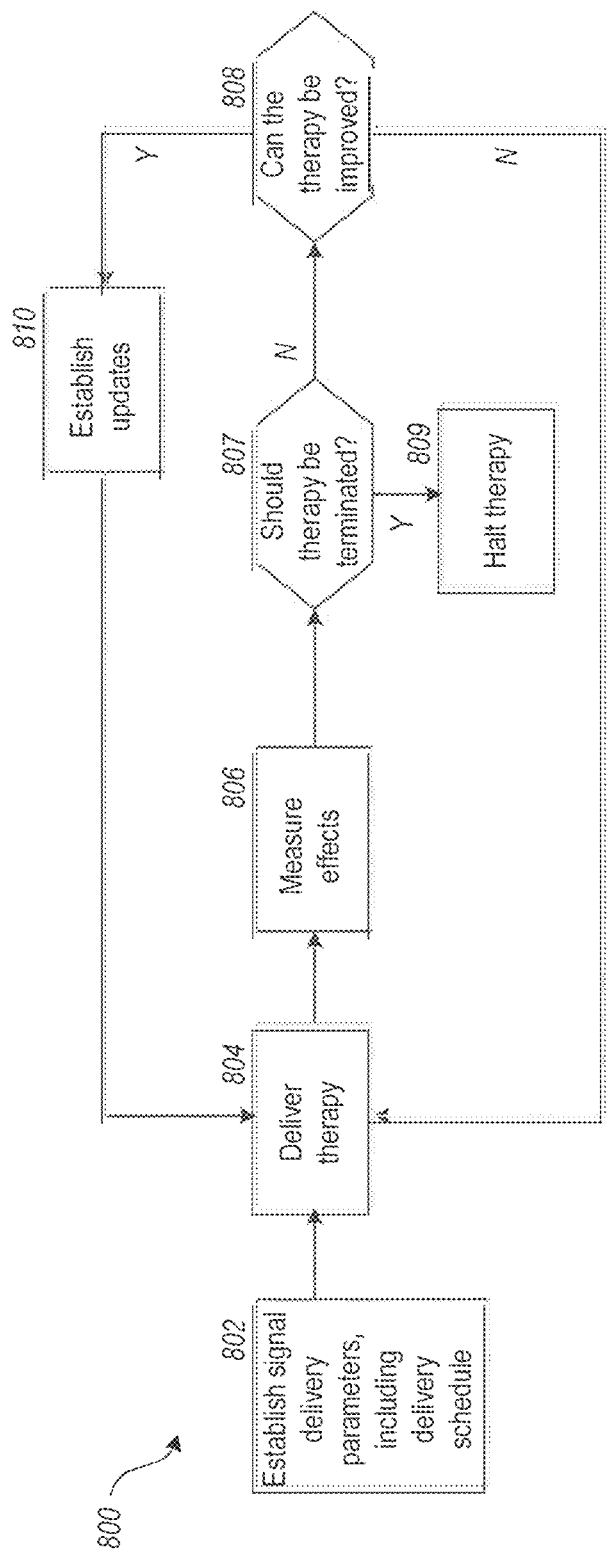
FIG. 8 is a flow diagram illustrating a representative process for applying therapy using a feedback loop arrangement in accordance with systems and methods of the present technology.

FIG. 8 is a schematic block diagram illustrating a process 800 for delivering therapy based on feedback from the patient, in accordance with representative systems and methods of the present technology. This approach can be used with any of the signal delivery modalities described herein (e.g., signal delivered via one signal device or more than one, signals delivered to one target neural population or more than one). Block 802 includes establishing the signal delivery parameters, including the signal delivery schedule. For example, block 802 can include establishing a continuous therapy regimen, in which the patient receives a therapy signal 24 hours a day, 7 days a week. In other representative systems and methods, the therapy signal may be delivered in accordance with a duty cycle. In still further representative systems and methods, the therapy signal may be delivered in accordance with a schedule that is tied to the patient's eating behavior. For example, the patient can receive therapy for one hour before and after a meal, as well as during the meal. The patient can activate the therapy manually, or, for example, if the patient is on a more or less fixed schedule, the therapy can automatically be activated via a timer so as to be delivered before, during and after the meal. Depending on the patient, the foregoing time periods can be adjusted (e.g., to be other than one hour before and/or one hour after), and/or one or two of the time periods can be eliminated.

The additional signal delivery parameters include signal frequency, amplitude, pulse width, and other waveform parameters, e.g., interpulse interval or interphase interval. The signal delivery parameters can further include which, among multiple possible electrodes or contacts, are activated at any particular time.

At block 804, the therapy is delivered, in accordance with the signal delivery schedule and other parameters described above. In block 806, the effects of the therapy on the patient are detected. For example, block 806 can include detecting a serum blood glucose level, at a particular point in time. In other representative systems and methods, detecting the effects of the therapy can include obtaining longer term measurements. For example, an A1C measurement is typically an average of A1C protein levels taken over a longer period of time, for example, three to four months. In representative applications, a 5% A1C level is considered normal, and levels above 6% trigger an evaluation, as described below. Representative systems and methods can include detecting or measuring other parameters, in addition to or in lieu of blood glucose—for example, insulin levels and/or blood pressure.

In any of the foregoing examples, the measured effects are then used to determine: whether the therapy is to be continued (block 807) and whether the therapy can be improved (block 808). If the therapy is to be discontinued (e.g., if the measured effects include an unsafe or otherwise undesirable effect), the therapy is halted at block 809. If not, then if the therapy can be improved (e.g., optimized), block 810 includes establishing updates for the therapy, and the process returns to block 804 to continue delivering therapy in accordance with the updated parameters. If, at block 808, the therapy is determined to be optimized (or is otherwise not to be changed), then the process returns to block 804 without establishing the updates identified at block 810.

The process 800 described above can be carried out in an automated fashion, or with a "person in the loop." For example, a practitioner can determine whether the therapy can be improved at block 808, and can establish the updates at block 810 if the therapy can be improved. In other representative methods, the process can be more automated. For example, the patient can use a constant glucose monitor that continuously monitors the patient's blood glucose level and communicates the measurements to an internal or external processor (e.g., an implanted pulse generator, or a phone-based app or other external device). When delivering results to an external processor, the system can use Bluetooth or another suitable wireless communication protocol. In any of these representative systems and methods, the system can automatically determine whether or not to change the signal parameters at block 808, and can automatically establish proposed updates at block 810. The updates can be based on historical data for the particular patient, and/or historical data for a larger patient population having the same or similar indications.

In at least some representative systems and methods, the frequency of the signal can determine the effect of the signal on the patient's physiology. For example, some frequencies may affect the patient's production of insulin, and others may affect the patient's storage of glucose. Generally, high frequency signals (e.g., above about 1200 Hz) can have an inhibitory effect, while lower frequency signals can have an excitatory effect. The effects may be limited to the specific neural populations to which the signals are directed. Accordingly, if the neural population is inhibitory (e.g., an inhibitory interneuron), an excitatory effect on an inhibitory neural population can produce an overall inhibitory physiological effect on the patient.

By selecting and manipulating the parameters described herein, the disclosed techniques can affect both insulin levels and the patient's glucose storage rates. By controlling both variables, these techniques can more accurately control the patient's blood sugar levels, and therefore more accurately control the patient's T2D. This approach can provide significant advantages over existing techniques for addressing T2D. For example, current techniques include administering insulin to the patent to reduce blood sugar levels. While this approach can have an acute benefit of reducing blood sugar levels, over the long term, it may actually worsen the patient's disease state.

The assignee of the present application has conducted clinical studies with patient's suffering from painful diabetic neuropathy (PDN). The primary purpose of the studies is to obtain data regarding the ability of electrical stimulation therapies to address the pain experienced by PDN patients. However, preliminary results of the study appear to suggest that, in addition to addressing PDN, the electrical stimulation therapy may be effective for addressing T2D. More specifically, 20% of patient's receiving electrical stimulation therapy in accordance with the foregoing parameters reported a significant reduction in A1C levels (e.g., in a range of 15%-23% reduction) over the course of three months of treatment. Patients who did not receive the electrical stimulation during the study did not indicate an A1C reduction. The patient's received a 10 kHz signal, with 30 microsecond anodic/cathodic biphasic pulses. The therapy was delivered from electrodes located at the T9-T10 vertebra level.

These preliminary results suggest that A1C reduction is achievable via electrical stimulation having frequencies in the ranges disclosed herein, and that tailoring the therapy delivery parameters more specifically to A1C reduction (rather than pain reduction) may further improve the results. For example, the therapy in the clinical study described above was delivered via electrodes at vertebral levels of approximately T9-T10 to address the patient's pain, While therapy directed to these locations reduced A1C levels, further reduction may be achieved at more cephalad vertebral levels (e.g., T4-T6) to provide better results for T2D patients.

More generally, electrical stimulation may be applied directly to the T2-T12 region, an organ, and/or another target tissue, or it may be applied in close proximity to the T2-T12 region, an organ, and/or another target tissue (i.e., close enough for neurons at the T2-T12 region, an organ, and/or another target tissue to receive the electrical signal). For example, electrical stimulation can be applied at or proximate to a target location in the T2-T12 region. As another example, the electrical stimulation can be applied to other neural tissue such as peripheral nerves corresponding to the T2-T12 region (e.g., sympathetic nerves). For example, electrical stimulation can be applied to the vagal nerve, such as the hepatic branch of the vagus nerve. Stimulation at the hepatic branch may increase activity of glycogen synthase, an enzyme involved in glucose metabolism, such as the conversion of glucose into glycogen.

For some conditions, electrical stimulation may be applied to a single target tissue or organ. For other conditions, electrical stimulation may be applied to the T2-T12 region, multiple organs, and/or multiple other target tissues. For example, where the patient condition is a blood glucose abnormality, stimulation may be applied to the T9 and/or T10 region, a nerve and/or a target tissue corresponding to T9 and/or T10, an organ corresponding to T9 and/or T10, or a combination thereof. In accordance with the present technology, electrical stimulation parameters may be configured so as to not result in the patient experiencing paresthesia.

The therapeutic modulation signal can operate on the targeted organ or organs in accordance with any of a number of mechanisms. For example, the therapeutic modulation signal can have an effect on a network of neurons, rather than an effect on a particular neuron. This network effect can in turn operate to reduce and/or otherwise inhibit one or more effects of the sympathetic nervous system described above. The foregoing mechanisms of action can have a cascading effect on other systems. For example, the effect of inhibiting the sympathetic nervous system can be indirect. As a result of this indirect effect, the ultimate effect on the organ may not occur instantaneously, but rather may take time (e.g., days) to develop, in response to a modulation signal that is applied to the patient for over a similar period of time (e.g., days).

A variety of suitable devices for administering an electrical signal to the T2-T12 region, an organ, and/or another target tissue are described in greater detail above under Heading 3.0 and may also be described in the references incorporated by reference herein. Examples of devices for administering an electrical signal that can treat T2D, reduce HbA1c levels, and/or treat pain are disclosed in U.S. Pat. Nos. 8,694,108 and 8,355,797, both of which are incorporated herein by reference in their entireties, and attached as Appendices H and D. For example, applying electrical stimulation can be carried out using suitable devices and programming modules specifically programmed to carry out any of the methods described herein. For example, the device can comprise a lead, wherein the lead in turn comprises an electrode. In representative methods, administering electrical stimulation comprises a positioning step (e.g., placing the lead such that an electrode is in proximity to the sacral region, an organ, and/or another target tissue) and a stimulation step (e.g., transmitting an electrical signal to the electrode). In representative systems and methods, a device that is used for applying an electrical signal to the spinal cord may be repurposed with or without modifications to administer an electrical signal to another target tissue or organ, e.g., at the T2-T12 region, a cortical, sub-cortical, intra-cortical, or peripheral target. For example, other target tissues or organs include the hypothalamus, brainstem, the limbic system, the cerebral cortex, the vagus nerve, and other direct end organs. As such, any of the herein described systems, subsystems, and/or sub-components serve as means for performing any of the herein described methods.

Many of the representative systems and methods described above were described in the context of treating a blood glucose abnormality with modulation signals applied to the T2-T12 vertebral levels, such as T9 and/or T10. T2D represents an example indication that can be treated with modulation applied at this location. In representative systems and methods, modulation signals having parameters (e.g., frequency, pulse width, amplitude, and/or duty cycle) generally similar to those described above can be applied to other patient locations, to address other indications.

The methods disclosed herein include and encompass, in addition to methods of making and using the disclosed devices and systems, methods of instructing others to make and use the disclosed devices and systems. For example, a representative method includes treating a patient's blood glucose abnormality by applying an electrical signal to the patient's T2-T12 region, with the electrical signal having parameters as disclosed throughout the present application, for example, a frequency in a range of from about 1.2 kHz to about 100 kHz, a pulse width in a pulse width range of one microsecond or less to 416 microseconds, and an amplitude in an amplitude range of 0.1 mA to 20 mA. The duty cycle (when less than 100%), can be between 5% and 75%, for example 60%-75%, 40%-60% (e.g., 50%), 25%-50%, or 10%-20%.

A representative method includes programming a device (or instructing programming of a device) to deliver electrical stimulation therapy in accordance with any of the foregoing parameters. Accordingly, any and all methods of use and manufacture disclosed herein also fully disclose and enable corresponding methods of instructing such methods of use and manufacture.

From the foregoing, it will be appreciated that representative systems and methods of the present technology have been described herein for purposes of illustration, but that various modifications may be made without deviating from the technology. As described above, signals having the foregoing characteristics can provide therapeutic benefits for patients having T2D, when stimulation is applied at T9 and/or T10. At other target locations, the electrical signal can have a more significant and/or targeted effect, e.g., when the electrical signal is directed to specific neurons or neural populations associated with specific organs that are enervated by nerves exiting the spinal cord at vertebral levels from about T2 to about T12, as described above. In representative systems and methods, the present technology can be used to address one or more pain indications, such as those described in the references incorporated by reference, besides and/or in addition to T2D.

The methods, systems, and devices described above may, in addition to treating the blood glucose abnormality, be used to deliver a number of suitable therapies, e.g., paresthesia-based therapies and/or paresthesia-free therapies, for patients experiencing pain and/or diseases or conditions other than the blood glucose abnormality, such as nausea, motility, and/or Homer syndrome, amongst others. Examples of such therapies and associated methods, systems, and devices are described in U.S. Patent Publication Nos. 2009/0204173 and 2010/0274314, the respective disclosures of which are herein incorporated by reference in their entireties, and attached as Appendices G and Certain aspects of the technology described in the context of particular representative systems and methods may be combined or eliminated in other representative systems and methods. For example, many of the representative systems and methods described above refer to delivery of the electrical therapy signal using two or more leads. In representative systems and methods, the electrical therapy signals described herein can be delivered with one lead, or more than one lead, and includes the leads described herein and those described in the references incorporated herein. In addition, while advantages associated with representative systems and methods of the technology have been described in the context of those systems and methods, other systems and methods may also exhibit such advantages, and not all systems and methods need necessarily exhibit such advantages to all within the scope of the present technology. Accordingly, the disclosure and associated technology can encompass other embodiments not expressly shown or described herein.

To the extent any materials incorporated by reference herein conflict with the present disclosure, the present disclosure controls.

5.0 Representative Examples

The following examples are provided to further illustrate representative systems and methods of the present technology and are not to be interpreted as limiting the scope of the present technology. To the extent that certain representative systems and methods or features thereof are mentioned, it is merely for purposes of illustration and, unless otherwise specified, is not intended to limit the present technology. One skilled in the art may develop equivalent means without the exercise of inventive capacity and without departing from the scope of the present technology. It will be understood that many variations can be made in the procedures herein described while still remaining within the bounds of the present technology. Such variations are intended to be included within the scope of the presently disclosed technology. As such, representative systems and methods of the presently disclosed technology are described in the following clauses.

1. A method for treating a patient having a blood glucose abnormality, comprising:
    based at least in part on a patient indication of a blood glucose abnormality, positioning at least one implantable signal delivery device proximate to a target location at the patient's spinal cord within a vertebral range of from about C8 to about T12; and
    directing an electrical signal to the target location via the implantable signal delivery device, wherein the electrical signal has a frequency in a frequency range of from 1.2 kHz to 100 kHz.

2. The method of clause 1 wherein the blood glucose abnormality includes type 2 diabetes (T2D) and/or metabolic syndrome.

3. The method of any of the foregoing clauses wherein the target location is along a longitudinal midline of the patient's spinal cord.

4. The method of clause any of the foregoing clauses wherein the at least one implantable signal delivery device is a paddle lead.

5. The method of clause any of the foregoing clauses wherein the electrical signal has a frequency of about 10 kHz.

6. The method of clause 5 wherein the electrical signal has a pulse width of about 30 microseconds.

7. The method of clause 6 wherein the electrical signal has an amplitude from about 20% of the patient's sensory threshold to about 90% of the patient's sensory threshold.

8. The method of clause 7 wherein the target location is from T4 to T6.

9. The method of clause 8 wherein the electrical signal inhibits one or more of the patient's sympathetic nerves associated with an organ selected from the group consisting of the patient's stomach, liver, pancreas, and one or more adrenal glands.

10. The method of clause 9 wherein the one or more sympathetic nerves are supplied by the patient's celiac ganglion.

11. The method of clause 7 wherein the target location is from T7 to T12.

12. The method of clause 11 wherein the electrical signal inhibits one or more of the patient's sympathetic nerves associated with an organ selected from the group consisting of the patient's stomach, duodenum, jejunum, ileum, and large intestine.

13. The method of clause 12 wherein the one or more sympathetic nerves are supplied by the patient's celiac ganglion and/or superior mesenteric ganglia.

14. The method of clause 12 wherein the electrical signal further comprises a duty cycling period having an on cycle and an off cycle.

15. The method of clause 14 wherein the organ is the patient's stomach, and wherein the on cycle is about 20 seconds, and the off cycle is about 20 seconds.

16. The method of clause 14 wherein the organ is the patient's duodenum, and wherein the on cycle is about 5 seconds, and the off cycle is about 5 seconds.

17. The method of clause 14 wherein the organ is the patient's jejunum, and wherein the on cycle is about 5.5 seconds, and the off cycle is about 5.5 seconds.

18. The method of clause 14 wherein the organ is the patient's ileum, and wherein the on cycle is about 7.5 seconds, and the off cycle is about 7.5 seconds.

19. The method of clause 14 wherein the organ is the patient's large intestine, and wherein the on cycle is about 10 seconds, the off cycle is about 10 seconds.

20. The method of any of the foregoing clauses wherein the electrical signal is delivered to the target location while the patient is prandial.

21. The method of clause 20 wherein the electrical signal is delivered for a time within a time period of from about 30 minutes and about 120 minutes.

22. The method of clause any of the foregoing clauses wherein the patient's blood glucose level is reduced by at least about 10%, at least about 15%, at least about 20%, at least about 25%, at least about 30%, at least about 35%, at least about 40%, at least about 45%, or at least about 50% following delivery of the electrical signal.

23. The method of clause any of the foregoing clauses wherein directing the electrical signal reduces a level of HbA1c in the patient.

24. The method of clause 23 wherein the patient's HbA1c level is reduced by at least about 1%, at least about 1.5%, at least about 2%, at least about 2.5%, at least about 3%, at least about 3.5%, at least about 4%, at least about 4.5%, at least about 5%, at least about 6%, at least about 7%, at least about 8%, at least about 9%, or at least about 10% following delivery of the electrical signal.

25. The method of any of the foregoing clauses wherein directing the electrical signal includes directing the electrical signal to lamina X of the patient's spinal cord.

26. The method of clause 25 wherein the electrical signal is directed to lamina X of the patient's spinal cord via conduction of the patient's cerebral spinal fluid at the patient's dorsal median sulcus or via one or more of laminae I-1X.

27. The method of clause any of the foregoing clauses wherein the electrical signal inhibits one or more of the patient's sympathetic nerves to promote glucose uptake in the patient's liver and/or lower the patient's post-prandial blood glucose levels.

28. The method of clause any of the foregoing clauses, further comprising:
monitoring the patient's blood glucose abnormality by measuring the patient's blood glucose level; and
in response to results obtained from monitoring the patient's blood glucose abnormality, performing at least one of the following processes:
  (a) adjusting at least one signal delivery parameter in accordance with which the electrical signal is directed to the target location, wherein the signal delivery parameter is at least one of frequency, amplitude, pulse width, or duty cycle,
  (b) continuing to deliver the electrical signal without adjusting at least one signal delivery parameter,
  (c) terminating delivery of the electrical signal.

29. A method for treating a patient, comprising:
based at least in part on a patient indication of T2D, positioning an implantable signal delivery device proximate to a target location at the patient's spinal cord in a vertebral range of from about C8 to about T12; and
directing an electrical signal to the target location via an implantable signal delivery device having a plurality of contacts, wherein the electrical signal has a frequency of 10 kHz, a pulse width of 30 microseconds, and an amplitude from about 20% of the patient's sensory threshold to about 90% of the patient's sensory threshold.

30. The method of clause 29 wherein the target location is along a longitudinal midline of the patient's spinal cord.

31. The method of clause 30 wherein the implantable signal delivery device is positioned to span a first portion of the patient's tissue on a first side of the patient's spinal cord midline and a second portion of the patient's tissue on a second side of the patient's spinal cord midline.

32. The method of clause 31 wherein at least one contact of the implanted signal delivery device is positioned proximate to the first portion and at least one contact is positioned proximate to the second portion.

33. The method of clause 29 wherein the target location is from T4 to T6.

34. The method of clause 33 wherein the electrical signal inhibits one or more sympathetic nerves associated with an organ selected from the group consisting of the patient's stomach, liver, pancreas, and one or more adrenal glands.

35. The method of clause 34 wherein the one or more sympathetic nerves are supplied by the patient's celiac ganglion.

36. The method of clause 29 wherein the target location is from T7 to T12.

37. The method of clause 36 wherein the electrical signal inhibits one or more of the patient's sympathetic nerves associated with an organ selected from the group consisting of the patient's stomach, duodenum, jejunum, ileum, and large intestine.

38. The method of clause 37 wherein the one or more sympathetic nerves are supplied by the patient's celiac ganglion and/or superior mesenteric ganglia.

39. The method of clause 37 wherein the electrical signal has a duty cycling period with an on cycle and an off cycle.

40. The method of clause 39 wherein the organ is the patient's stomach, and wherein the on cycle is about 20 seconds, and the off cycle is about 20 seconds, e.g., to target the sympathetic nerves that innervate the patient's stomach.

41. The method of clause 39 wherein the organ is the patient's duodenum, and wherein the on cycle is about 5 seconds, and the off cycle is about 5 seconds, e.g., to target the sympathetic nerves that innervate the patient's duodenum.

42. The method of clause 39 wherein the organ is the patient's jejunum, and wherein the on cycle is about 5.5 seconds, and the off cycle is about 5.5 seconds, e.g., to target the sympathetic nerves that innervate the patient's jejunum.

43. The method of clause 39 wherein the organ is the patient's ileum, and wherein the on cycle is about 7.5 seconds, and the off cycle is about 7.5 seconds, e.g., to target the sympathetic nerves that innervate the patient's ileum.

44. The method of clause 39 wherein the organ is the patient's large intestine, and wherein the on cycle is about 10 seconds, and the off cycle is about 10 seconds, e.g., to target the sympathetic nerves that innervate the patient's large intestine.

45. The method of clause 30 wherein the electrical signal is delivered to the target location simultaneously by contacts on opposing sides of the patient's spinal cord midline.

46. The method of any of clauses 29-45 wherein the electrical signal is delivered to the target location while the patient is prandial.

47. The method of clause 46 wherein the electrical signal is delivered for between about 30 minutes and about 120 minutes.

48. The method of any of clauses 29-47 wherein the patient's blood glucose level is reduced by at least about 10%, at least about 15%, at least about 20%, at least about 25%, at least about 30%, at least about 35%, at least about 40%, at least about 45%, or at least about 50% following delivery of the electrical signal.

49. The method of clause any of clauses 29-48 wherein directing the electrical signal reduces a level of HbA1c in the patient.

50. The method of clause 49 wherein the patient's HbA1c level is reduced by at least about 1%, at least about 1.5%, at least about 2%, at least about 2.5%, at least about 3%, at least about 3.5%, at least about 4%, at least about 4.5%, at least about 5%, at least about 6%, at least about 7%, at least about 8%, at least about 9%, or at least about 10% following delivery of the electrical signal.

51. The method of any of clauses 29-50 wherein directing the electrical signal includes directing the electrical signal to lamina X of the patient's spinal cord.

52. The method of clause 51 wherein the electrical signal is directed to lamina X of the patient's spinal cord via conduction of the patient's cerebral spinal fluid at the patient's dorsal median sulcus or via one or more of laminae I-IX.

53. The method of any of clauses 29-52 wherein the electrical signal inhibits one or more of the patient's sympathetic nerves to promote glucose uptake in the patient's liver and/or lower the patient's post-prandial blood glucose levels.

54. The method of any of clauses 29-53, further comprising:
monitoring the patient's T2D by measuring the patient's blood glucose levels; and
in response to results obtained from monitoring the patient's T2D, adjusting at least one signal delivery parameter in accordance with which the electrical signal is applied to the target location, wherein the signal delivery parameter is selected from the group consisting of frequency, amplitude, pulse width, and duty cycle.

55. A method for treating a patient, comprising:
based at least in part on a patient indication of T2D, positioning at least one implantable signal delivery device proximate to a target location at the patient's spinal cord within a vertebral range of from about C8 to about T12;
directing an electrical signal to the target location via the at least one implantable signal delivery device to modify the patient's (a) blood glucose level or (b) insulin level, or (c) both (a) and (b), wherein the electrical signal has a frequency in a frequency range of from 1.2 kHz to 100 kHz.

56. The method of clause 55 wherein the at least one implantable signal delivery device includes a first set of contacts and a second set of contacts.

57. The method of clause 56 wherein the first set of contacts are positioned on a first side of the patient's spinal cord midline and the second set of contacts are positioned on a second side of the patient's spinal cord midline.

58. The method of clause 57 wherein the at least one implantable signal delivery device is a paddle lead.

59. The method of clause 58 wherein the first set of contacts are on a first side of the paddle lead and the second set of contacts are on a second side of the paddle lead.

60. A method for treating a patient, comprising:
based at least in part on a patient indication of T2D, positioning at least one first contact proximate to a first target location at the patient's spinal cord within a vertebral range of about T2 to about T12, and placing at least one second contact proximate to a second target location at the patient's spinal cord within the vertebral range of about T2 to about T12; and
directing a first electrical signal to the first target location via the at least one first contact and directing a second electrical signal to the second target location via the at least one second, wherein the first and second electrical signals each have a frequency in a frequency range of from 1.2 kHz to 100 kHz.

61. The method of clause 60 wherein the at least one first contact is carried by a first implantable signal delivery device, and wherein the at least one second contact is carried by a second implantable signal delivery device.

62. The method of any of clauses 60-61 wherein the at least one first contact and the at least one second contact are carried by a single implantable signal delivery device, and wherein the single signal delivery device includes a paddle.

63. The method of any of clauses 60-62 wherein the at least one first contact is positioned on a first side of the patient's spinal cord midline and the at least one second contact is positioned on a second side of the patient's spinal cord midline.

64. The method of clause 63 wherein the at least one first contact includes a plurality of first contacts positioned longitudinally along the first side of the midline, and wherein the at least one second contact includes a plurality of second contacts positioned longitudinally along the second side of the midline.

65. The method of any of clauses 60-64 wherein the first target location is proximate to a first thoracic vertebrae and the second target location is proximate to a second thoracic vertebrae different from the first thoracic vertebrae.

66. A system for treating a patient having a blood glucose abnormality, comprising:
a signal delivery device implantable in the epidural space of the patient's spinal cord region;
a pulse generator electrically coupleable to the signal delivery device;
a patient sensor; and
a machine-readable medium operatively coupled to the patient sensor and the pulse generator, the machine-readable medium having machine-readable instructions that, when executed:
receive an input from the patient sensor corresponding to an indication of at least one of a patient blood glucose level or a patient insulin level; and
in response to the input, change at least one parameter in accordance with which the pulse generator directs an electrical signal to the implantable signal delivery device, wherein the electrical signal has a frequency in a frequency range of from 1.2 kHz to 100 kHz.

67. The system of clause 66 wherein the patient sensor is an insulin sensor.

68. The system of clause 66 wherein the patient sensor is a blood glucose sensor.

69. The system of clause 66 wherein the patient sensor is an HbA1C sensor.

70. The system of any of clauses 66-69 wherein the electrical signal has a duty cycling period with an on cycle and an off cycle, and wherein the on and off cycles are correlated with the patient's normal slow wave frequency.

71. The system of clause 70 wherein the on cycle is about 20 seconds, the off cycle is about 20 seconds, and the normal slow wave frequency is about 3 waves per minute, e.g., to target the sympathetic nerves that innervate the patient's stomach.

72. The system of clause 70 wherein the on cycle is about 5 seconds, the off cycle is about 5 seconds, and the normal slow wave frequency is about 12 waves per minute, e.g., to target the sympathetic nerves that innervate the patient's duodenum.

73. The system of clause 70 wherein the on cycle is about 5.5 seconds, the off cycle is about 5.5 seconds, and the normal slow wave frequency is about 11 waves per minute, e.g., to target the sympathetic nerves that innervate the patient's jejunum.

74. The system of clause 70 wherein the on cycle is about 7.5 seconds, the off cycle is about 7.5 seconds, and the normal slow wave frequency is about 8 waves per minute, e.g., to target the sympathetic nerves that innervate the patient's ileum.

75. The system of clause 70 wherein the on cycle is about 10 seconds, the off cycle is about 10 seconds, and the normal slow wave frequency is about 6 waves per minute, e.g., to target the sympathetic nerves that innervate the patient's large intestine.

76. The system of any of clauses 66-75 wherein the electrical signal is delivered to the target location while the patient is prandial.

77. The system of any of clauses 66-76 wherein the at least one parameter includes at least one of frequency, amplitude, pulse width, or duty cycle.

78. The system of any of clauses 66-77 wherein the machine-readable instructions, when executed terminate delivery of the electrical signal in response to the input.

79. The system of any of clauses 66-78 wherein the electrical signal has an amplitude in an amplitude range of from 0.1 mA to 20 mA.

80. The system of any of clauses 66-78 wherein the electrical signal has an amplitude in an amplitude range of from 0.5 mA to 10 mA.

81. An electrical signal having a frequency in a frequency range of from 1.2 kHz to 100 kHz for use in treating type 2 diabetes (T2D), wherein the electrical signal is generated by a pulse generator and directed to an implantable signal delivery device.

82. The electrical signal of clause 81 wherein the frequency range is from 2 kHz to 50 kHz.

83. The electrical signal of clause 81 wherein the frequency range is from 3 kHz to 20 kHz.

84. The electrical signal of clause 81 wherein the frequency range is from 3 kHz to 10 kHz.

85. The electrical signal of clause 81 wherein the frequency is 10 kHz.

86. The electrical signal of any of clauses 81-85 wherein a pulse width of the signal is in a pulse width range of from 1 microsecond to 416 microseconds.

87. The electrical signal of any of clauses 81-85 wherein a pulse width of the signal is 5 microseconds or less.

88. The electrical signal of any of clauses 81-85 wherein a pulse width of the signal is 30 microseconds.

89. The electrical signal of any of clauses 81-88 wherein an amplitude of the signal is in an amplitude range of from 0.1 mA to 20 mA.

90. The electrical signal of any of clauses 81-88 wherein an amplitude of the signal is in an amplitude range of from 0.5 mA to 10 mA.

91. The electrical signal any of clauses 81-88 wherein an amplitude of the signal is in an amplitude range of from 0.5 mA to 5 mA.

92. The electrical signal of any of clauses 81-91 wherein the implantable signal delivery device carries contacts positioned to direct the electrical signal to a target location at a patient's spinal cord.

93. The electrical signal of clause 81 wherein the frequency range is from 1.2 kHz to 100 kHz and wherein the electrical signal has a pulse width in a pulse width range of from 1 microsecond to 416 microseconds, and an amplitude in an amplitude range of from 0.5 mA to 15 mA.

94. The electrical signal of clause 81 wherein the frequency range is from 1.2 kHz to 50 kHz and wherein the electrical signal has a pulse width in a pulse width range of from 10 microseconds to 416 microseconds, and an amplitude in an amplitude range of from 0.5 mA to 10 mA.

95. The electrical signal of clause 81 wherein the frequency range is from 1.2 kHz to 25 kHz and wherein the electrical signal has a pulse width in a pulse width range of from 20 microseconds to 416 microseconds, and an amplitude in an amplitude range of from 0.5 mA to 7.5 mA.

96. The electrical signal of clause 81 wherein the frequency range is from 5 kHz to 25 kHz and wherein the electrical signal has a pulse width in a pulse width range of from 20 microseconds to 100 microseconds, and an amplitude in an amplitude range of from 1 mA to 7.5 mA.

97. The electrical signal of clause 81 wherein the frequency is 10 kHz and wherein the electrical signal has a pulse width of 30 microseconds, and an amplitude in an amplitude range of from 0.5 mA to 5 mA.

98. A method for treating a patient having a blood glucose abnormality, comprising:
positioning at least one implantable signal delivery device proximate to a target location at the patient's spinal cord within a vertebral range of from about C8 to about T12; and
directing an electrical signal to the target location via the implantable signal delivery device, wherein the electrical signal has a frequency in a frequency range of from 1.2 kHz to 100 kHz.

We claim:

1. A method for treating a patient having a blood glucose abnormality, comprising:
programming an implantable signal generator to deliver an electrical signal having a frequency in a frequency range of from 1.2 kHz to 100 kHz to the patient's spinal cord region, via at least one implanted signal delivery device positioned proximate to a target location within a vertebral range of from about C8 to about T12, for a duration of between about 30 minutes and about 120 minutes while the patient is prandial,
wherein the electrical signal modulates neurons of the intermediolateral cell column to treat the blood glucose abnormality of the patient.

2. The method of claim 1 wherein the blood glucose abnormality includes type 2 diabetes (T2D).

3. The method of claim 1 wherein the target location is offset from a longitudinal midline of the patient's spinal cord.

4. The method of claim 1 wherein the electrical signal has a frequency in a frequency range of from 5 kHz to 50 kHz.

5. The method of claim 1 wherein the electrical signal has a frequency in a frequency range of from 5 kHz to 15 kHz.

6. The method of claim 1 wherein the electrical signal has a pulse width in a pulse width range of from 10 microseconds to 166 microseconds.

7. The method of claim 1 wherein the electrical signal has an amplitude from about 20% of the patient's sensory threshold to about 90% of the patient's sensory threshold.

8. The method of claim 1 wherein the target location is from T4 to T6.

9. The method of claim 8 wherein the electrical signal inhibits one or more of the patient's sympathetic nerves associated with the patient's liver.

10. The method of claim 1 wherein the neurons include sympathetic preganglionic neurons.

11. The method of claim 10 wherein the electrical signal stimulates sympathetic interneurons that project to the sympathetic preganglionic neurons.

12. The method of claim 11 wherein the sympathetic interneurons are located in lamina X of the patient's spinal cord.

13. The method of claim 1 wherein the electrical signal promotes glucose uptake in the patient's liver and/or lowers the patient's post-prandial blood glucose levels.

14. The method of claim 1 wherein the electrical signal reduces the patient's blood glucose level.

15. The method of claim 1 wherein the electrical signal reduces a level of HbA1c in the patient.

16. The method of claim 1 wherein the electrical signal is a first electrical signal, and wherein programming the implantable signal generator includes programming the implantable signal generator to deliver a second electrical signal different than the first electrical signal during a post-prandial phase after the duration of between about 30 minutes and about 120 minutes.

17. A method for treating a patient having a blood glucose abnormality, comprising:
programming an implantable signal generator to deliver an electrical signal having a frequency in a frequency range of from 1.2 kHz to 100 kHz to the patient's spinal cord region, via at least one implanted signal delivery device positioned proximate to a target location within a vertebral range of from about C8 to about T12, for a duration of between about 30 minutes and about 120 minutes while the patient is prandial.

18. The method of claim 17 wherein the electrical signal is a first electrical signal, and wherein programming the implantable signal generator includes programming the implantable signal generator to deliver a second electrical signal different than the first electrical signal during a post-prandial phase after the duration of between about 30 minutes and about 120 minutes.

19. The method of claim 18 wherein the beginning of the prandial event is detected via one or more sensors configured to monitor the patient's blood glucose levels.

20. The method of claim 17 wherein programming the implantable signal generator includes programming the implantable signal generator to automatically deliver the electrical signal after detecting a beginning of a prandial event.

21. The method of claim 17 wherein the blood glucose abnormality includes type 2 diabetes (T2D).

22. The method of claim 17 wherein the target location is offset from a longitudinal midline of the patient's spinal cord.

23. The method of claim 17 wherein the electrical signal has a frequency in a frequency range of from 5 kHz to 50 kHz.

24. The method of claim 17 wherein the electrical signal has a frequency in a frequency range of from 5 kHz to 15 kHz.

25. The method of claim 17 wherein the electrical signal has a pulse width in a pulse width range of from 10 microseconds to 166 microseconds.

26. The method of claim 17 wherein the electrical signal has an amplitude from about 20% of the patient's sensory threshold to about 90% of the patient's sensory threshold.

27. The method of claim 17 wherein the target location is from T4 to T6.

28. The method of claim 27 wherein the electrical signal inhibits one or more of the patient's sympathetic nerves associated with the patient's liver.

29. The method of claim 17 wherein the electrical signal modulates sympathetic preganglionic neurons.

30. The method of claim 29 wherein the electrical signal stimulates sympathetic interneurons that project to the sympathetic preganglionic neurons.

31. The method of claim 30 wherein the sympathetic interneurons are located in lamina X of the patient's spinal cord.

32. The method of claim 17 wherein the electrical signal promotes glucose uptake in the patient's liver and/or lowers the patient's post-prandial blood glucose levels.

33. The method of claim 17 wherein the electrical signal reduces the patient's blood glucose level.

34. The method of claim 17 wherein the electrical signal reduces a level of HbA1c in the patient.

* * * * *